(12) United States Patent
Ling et al.

(10) Patent No.: US 6,864,282 B2
(45) Date of Patent: Mar. 8, 2005

(54) 9,11-CYCLOENDOPEROXIDE PRO-DRUGS OF PROSTAGLANDIN ANALOGUES FOR TREATMENT OF OCULAR HYPERTENSION AND GLAUCOMA

(75) Inventors: Kah-Hiing John Ling, Newport Coast, CA (US); Wu Yang, Irvine, CA (US); Jinsong Ni, Foothill Ranch, CA (US); Haiqing Yuan, Irvine, CA (US); Diane D. S. Tang-Liu, Newport Beach, CA (US)

(73) Assignee: Allergan, Inc., Irvine, CA (US)

( * ) Notice: Subject to any disclaimer, the term of this patent is extended or adjusted under 35 U.S.C. 154(b) by 0 days.

(21) Appl. No.: 10/212,437

(22) Filed: Aug. 5, 2002

(65) Prior Publication Data

US 2004/0023954 A1 Feb. 5, 2004

(51) Int. Cl.[7] ..................... A61K 31/357; C07D 317/06
(52) U.S. Cl. ..................... 514/464; 514/452; 514/456; 514/466; 549/363; 549/443; 549/445; 549/446
(58) Field of Search ..................... 514/464, 452, 514/456, 466; 549/363, 443, 445, 446

(56) References Cited

U.S. PATENT DOCUMENTS

| | | | |
|---|---|---|---|
| 4,599,353 A | 7/1986 | Bito | |
| 5,422,368 A | 6/1995 | Stjernschantz | |
| 5,552,434 A | 9/1996 | Garst | |
| 5,767,154 A | 6/1998 | Woodward | |
| 6,329,426 B1 | 12/2001 | Ueno | |
| 6,342,524 B1 | 1/2002 | Hellberg | |

FOREIGN PATENT DOCUMENTS

WO   WO-02-12445   2/2002

OTHER PUBLICATIONS

Raz, Amiram, et al. Endoperoxides and Thromboxanes. Structural Determinants for Platelet Aggregation and Vasoconstriction, Biochimica Et Biophysica Acta, 1977, 305–311, vol.488, No. 2.
Gorman R. R., et al., Prostaglandis H1 and H2. Convenient Biochemical Synthesis and Isolation. Further Biological and Spectroscopic Characterization, Prostaglandins, Jun. 1977, 1043–1053, vol.13, No. 6.
Graff, G., et al., Identification of 15–Keto–9, 11–Peroxidoprosta–5, 13–Dienoic Acid as a Hematin–Catalyzed Decomposition Product of 15–Hydroperoxy–9, 11–Peroxidoprosta–5, 13–Dienoic Acid, Lipids, 1979, 334–342, vol.14, No. 4.
Diczfalusy, Ulf, et al., Enzymic Conversion of C21 Endoperoxides to Thromboxanes and Hydroxy Acids, Biochemica and Biophysical Research Communications, 1980, 1417–1423, vol.94, No. 4.
Leduc, Louis E., et al., Analogs of Arachidonic Acid Used to Evaluate Structural Determinants of Prostaglandin Receptor and Enzyme Specificities, Molecular Pharmacology, 1981, 242–247, vol.19, No. 2.
Abadji, V. et al., J. Med. Chem. 1994, 37, 1889–1893.
Ryan, W. J. et al., J. Med. Chem. 1997, 40, 3617–3625.
Corey, E.J. et al., Tetrahedron Lett. 1983, 24, 37–40.
Manna, S. et al., Tetrahedron Lett. 1983, 24, 33–36.
Corey, E.J. and Cheng, X.–M., The Logic of Chemical Synthesis; Wiley: New York, 1989; Chapter 12, pp. 312–357 and references therein.
Hla, T. and Neilson K., Proc Natl Acad Sci USA, 1992, 89: 7384–7388.
Suzuki–Yamamoto T., et al., FEBS Lett, 1999, 462: 335–340.
Jakobsson, P., et al., Proc. Natl. Acad Sci USA, 1999, 96: 7220–7225.
Nagata, A., et al., Proc Natl Acad Sci USA, 1991, 88: 4020–4024.
Miyata, A., et al., Eur. J. Biochem, 1994, 224: 273–279.
Miyata, A., et al., Biochem Biophys Res Commun, 1994, 200: 1728–1734.
Fredholm et al., Prostaglandins 1976, 11: 507–518.
Stringfellow et al., Prostaglandins 1978, 16: 901–910.
Seltzman et al., J. Med. Chem. 1997, 40: 3626–3634.
Dasse et al. Tetrahedron 2000, 56: 9195–9202.

*Primary Examiner*—Ba K. Trinh
(74) *Attorney, Agent, or Firm*—Gabor L. Szekeres; Carlos A. Fisher; Martin A. Voet

(57) ABSTRACT

9,11-Cycloendoperoxide derivatives of biologically active prostaglandin analogs, and particularly of the ocular hypotensive drugs Bimatoprost, Latanaprost, Unoprostone, Travoprost and prostaglandin $H_2$ 1-ethanolamide or of structurally closely related analogs, are pro-drugs which hydrolyze under physiological conditions to provide prostaglandin analogues that are capable of providing sustained ocular and other in vivo concentrations of the respective drugs. The compounds of the invention have the formula shown below where the variables have the meaning defined in the specification.

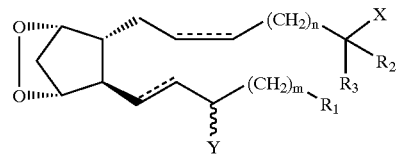

37 Claims, No Drawings

9,11-CYCLOENDOPEROXIDE PRO-DRUGS OF PROSTAGLANDIN ANALOGUES FOR TREATMENT OF OCULAR HYPERTENSION AND GLAUCOMA

BACKGROUND OF THE INVENTION

1. Field of the Invention

The present invention is in the field of prostaglandin and analog drugs. More particularly the present invention is in the field of prostaglandin analog drugs which are used for treatment of ocular hypertension, glaucoma or have other useful pharmacological properties. Still more particularly, the present invention is directed to pro-drugs of prostaglandin analogs which are used for treatment of ocular hypertension, glaucoma, have beneficial effects on platelet congregation, gastric ulceration, blood pressure regulation and inflammation.

2. Background Art

Several prostaglandin analogs are presently known for their ability to reduce intraocular pressure and can be used for treatment of glaucoma and related diseases of the eye. Among these the drugs known by the names Bimatoprost (U.S. Pat. No. 5,688,819) Latanoprost (U.S. Pat. Nos. 4,599, 353, 5,296,504, 5,422,368), Unoprostone (U.S. Pat. No. 6,329,426) and Travoprost (U.S. Pat. Nos. 5,631,287, 5,849, 792, 5,889,052, 6,011,062) are mentioned as important ones in current use, and are shown by chemical structure below. The conventional numbering of prostaglandins and like structures is indicated in connection with the formula of Bimatoprost.

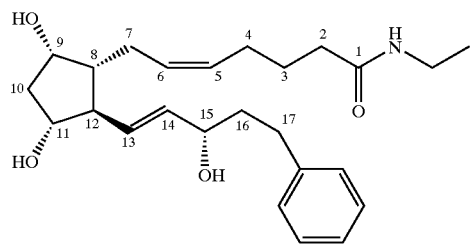

Bimatoprost

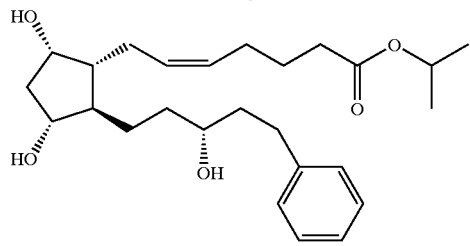

Latanoprost

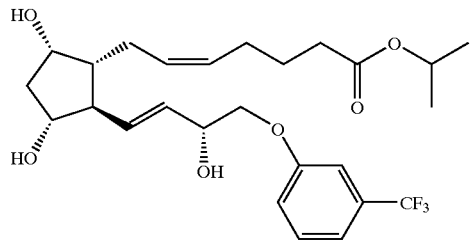

Travoprost

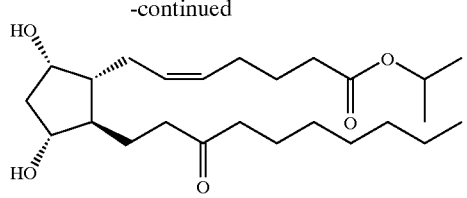

Unoprostone

SUMMARY OF THE INVENTION

In accordance with the present invention 9,11 cycloendoperoxide derivatives of biologically active prostaglandin analogs comprise pro-drugs which hydrolyze under physiological conditions to provide prostaglandin analogues that are capable of providing sustained ocular and other in vivo concentrations of biologically active prostaglandin analogues. See Fredholm et al., Prostaglandins 1976, 11, 507–518 and Stringfellow et al., Prostaglandins 1978, 16, 901–910).

The 9,11-cycloendoperoxide analogs of biologically active prostaglandins are, generally speaking, chemically stable and are converted to the active drugs Bimatoprost, Latanaprost, Unoprostone, Travoprost, and $H_2$ 1-ethanolamide or to structurally closely related analogs, as well as into other biologically active prostglandins, such as prostaglandins $D_2$, $E_2$, and $F_{2alpha}$, thromboxane and prostacyclin analogs, with ocular hypotensive and other biological activity. The thromboxane and prostacyclin analogues effect platelet aggregation and are expected to play a crucial role in preventing gastric ulceration by inhibiting gastric acid secretion, in blood pressure regulation by control of vascular tone, and in inflammation by inhibiting protease secretion of polymorphonuclear leucocytes.

In addition to being useful as pro-drugs which hydrolyze under physiologic condition to the corresponding drugs, the 9,11-cycloendoperoxides of the invention may per se have the biological activity of the corresponding drug into which they hydrolyze, and as such are expected to provide still better sustained physiological concentration of the therapeutic agent which they represent.

The 9,11-cycloendoperoxide pro-drugs of the present invention, in addition to undergoing hydrolysis to provide the corresponding biologically active prostaglandin analogs, also act as substrates to several naturally occurring enzymes which convert the 9,11-cycloendoperoxide pro-drugs into other biologically active analogs wherein the molecular structure is modified. These enzymatic reactions which occur in vivo can also be performed in vitro by utilizing the corresponding enzymes isolated from human or other mammalian organisms, and are illustrated below in Reaction Schemes 10 through 20.

The compounds of the invention are generally disclosed by Formula 1,

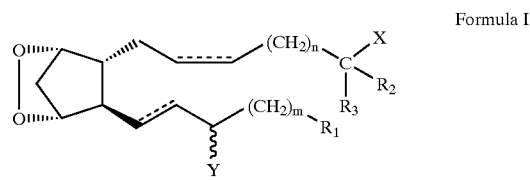

Formula I wherein the dashed lines represent the presence of a bond, or absence of a bond, wavy lines represent either alpha or beta configuration, solid triangles represent beta configuration and hatched lines represent alpha configuration;

n is an integer having the values of 1 to 6;

m is an integer having the values of 1 to 8;

X is $NH_2$, $N(R)_2$, NHR, or OR where R is hydrogen, $R_4$ or a $(CO)R_4$ group;

Y is =O, =S or OH, $OR_5$ or —$O(CO)R_5$ groups, said OH, $OR_5$ or $O(CO)R_5$ groups being attached to the adjacent carbon in alpha or beta configuration;

$R_1$ is H, $CH_3$, $R_7$, $OR_7$ or $SR_7$ where $R_7$ is an aliphatic, aromatic or heteroaromatic ring, said heteroaromatic ring having 1 to 3 heteroatoms selected from O, S, and N, said aliphatic, aromatic or heteroaromatic ring being optionally substituted with 1 to 3 $R_8$ groups where $R_8$ is F, Cl, Br, I, $NO_2$, $C_{1-6}$ alky, $C_{1-6}$ fluoro substituted alkyl, COOH, or $COOR_9$ where $R_9$ is alkyl of 1 to 6 carbons or $CH_2OCH_3$;

$R_2$ and $R_3$ together represent =O, =S, or independently are hydrogen or alkyl of 1 to 6 carbon atoms;

$R_4$ represents $(CH_2)_rOH$, $(CH_2)_rOCOR_9$ or $(CH_2)_rOR_9$ where r is an integer having the values 1 to 6, or $R_4$ represents saturated or unsaturated acyclic hydrocarbons having from 1 to 20 carbon atoms, or —$(CH_2)_qR_6$ where q is 0–10 and $R_6$ is an aliphatic, aromatic or heteroaromatic ring, said heteroaromatic ring having 1 to 3 heteroatoms selected from O, S, and N, said aliphatic, aromatic or heteroaromatic ring being optionally substituted with 1 to $R_8$ groups where $R_8$ is F, Cl, Br, I, $NO_2$, $C_{1-6}$ alky, $C_{1-6}$ fluoro substituted alkyl, COOH, $COOR_9$ where $R_9$ is alkyl of 1 to 6 carbons or $CH_2OCH_3$;

$R_5$ represents saturated or unsaturated acyclic hydrocarbons having from 1 to 20 carbon atoms, or —$(CH_2)_qR_6$, or a pharmaceutically acceptable salt of said compound.

DETAILED DESCRIPTION OF THE INVENTION

Definitions:

As used herein the term alkyl refers to and covers any and all groups which are known as normal alkyl, branched-chain alkyl, cycloalkyl and also cycloalkyl-alkyl. The term alkenyl refers to and covers normal alkenyl, branch-chained alkenyl and cycloalkenyl groups having one or more sites of unsaturation. When referring to saturated or unsaturated acyclic hydrocarbons, the term covers normal alkyl, normal alkenyl and normal alkynyl groups as well as branch-chained alkyl, branch-chained alkenyl and branch-chained alkynyl groups, the normal and branch-chained alkenyl and alkynyl groups having one or more sites of unsaturation.

A pharmaceutically acceptable salt may be prepared for any compound in this invention having a functionality capable of forming a salt, for example an acid or amine functionality. A pharmaceutically acceptable salt is any salt which retains the activity of the parent compound and does not impart any deleterious or untoward effect on the subject to which it is administered and in the context in which it is administered.

Pharmaceutically acceptable salts may be derived from organic or inorganic bases. The salt may be a mono or polyvalent ion. Of particular interest are the inorganic ions, sodium, potassium, calcium, and magnesium. Organic salts may be made with amines, particularly ammonium salts such as mono-, di- and trialkyl amines or ethanol amines. Salts may also be formed with caffeine, tromethamine and similar molecules. Where there is a nitrogen sufficiently basic as to be capable of forming acid addition salts, such may be formed with any inorganic or organic acids or alkylating agent such as methyl iodide. Preferred salts are those formed with inorganic acids such as hydrochloric acid, sulfuric acid or phosphoric acid. Any of a number of simple organic acids such as mono-, di- or tri-acid may also be used.

The compounds of the present invention are capable of existing as trans and cis (E and Z) isomers relative to the five-membered ring shown in the respective formulas, and relative to olefinic double bonds. Unless specific orientation of substituents relative to a double bond or the ring is indicated in the name of the respective compound, and/or by specific showing in the structural formula of the orientation of the substituents relative to the double bond or ring, the invention covers trans as well as cis isomers relative to each center that gives rise to such isomerism, as well as mixtures of trans and cis isomers.

The compounds of the present invention also contain one or more chiral centers and therefore may exist in enantiomeric and diastereomeric forms. Again, unless the name of a compound or its formula specifically describes or shows a specific enantiomer or diastereomer, the scope of the present invention is intended to cover all isomers per se, as well as mixtures of cis and trans isomers, mixtures of diastereomers and racemic mixtures of enantiomers (optical isomers) as well.

In the presently preferred compounds of the invention the variable n is 3, and the variable m is in the range or 1 to 6. The dotted line between carbons 5 and 6 as the numbering is shown on the structure depicting Bimatoprost, preferably represents a bond.

The variable Y preferably represents =O or OH, or $O(CO)R_5$, where $R_5$ is preferably alkyl of 1 to 6 carbons. Even more preferably Y is OH attached to the adjacent carbon with a bond of alpha orientation.

In the presently preferred compounds of the invention $R_1$ is methyl, phenyl, phenyl substituted in the phenyl group in the manner described in connection with Formula 1, or $R_1$ is O-phenyl, or O-phenyl substituted in the phenyl group in the manner described in connection with Formula 1. When $R_1$ is O-phenyl substituted in the phenyl group then the presently most preferred substituent is trifluoromethyl.

With respect to the group shown as $C(X)(R_2)(R_3)$ in Formula 1 the $R_2$ and $R_3$ groups preferably jointly form an oxo (=O) function, and the variable X is preferably OH, $OR_4$ or $NHR_4$. $R_4$ is preferably alkyl of 1 to 6 carbons, or $(CH_2)_rOH$ where most preferably r is an integer having the value 2.

The presently most preferred compounds of the invention are the 9,11-cycloendoperoxide pro-drugs structurally closely related to Bimatoprost, Latanapost, Unoprostone, Travoprost, Bimatoprost acid and of Prostaglandin $H_2$ 1-ethanolamide, the chemical structures of which are provided below. Although these structures show specific examples, they nevertheless generally show the 9,11-cycloendoperoxide moiety which can be introduced into the biologically active prostaglandin analogs by the enzymatic synthetic methods described below in detail. Numbers in parentheses next to the 9,11-cycloendoperoxides illustrated below refer to the specific compound numbers which are utilized in the specific description of examples and corresponding reaction schemes.

The enzymatic methods utilize the enzyme human COX-2 which can be obtained commercially from Cayman Chemical (Ann Arbor, Mich.). It was cloned in as described by Hla et al. in Proc. Natl. Acad. Sci. USA 1992, 89: 7384–7388, incorporated herein by reference. The enzyme was prepared by expression of a DNA clone encoding this enzyme in Baculovirus overexpression system in insect host cells (Sf21 cells).

The compounds on which the enzymatic syntheses utilizing the enzyme human COX-2 are performed can be prepared by chemical reactions and/or a combination of chemical and enzymatic reactions which are illustrated below, and by such modifications and adaptation of the chemical and/or enzymatic reactions which are within the skill of the practicing synthetic chemist in light of the present disclosure combined with general knowledge and available scientific and patent literature.

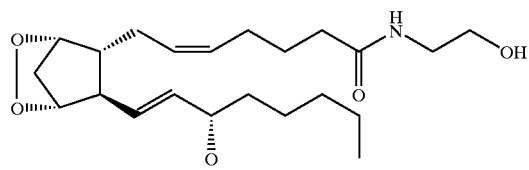

Prostaglandin H$_2$ 1-ethanolamide (17)

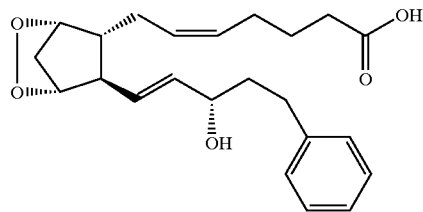

Bimatoprost acid 9,11-cycloendoperoxide (18)

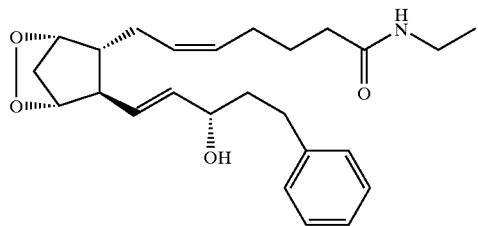

Bimatoprost 9,11-cycloendoperoxide (19)

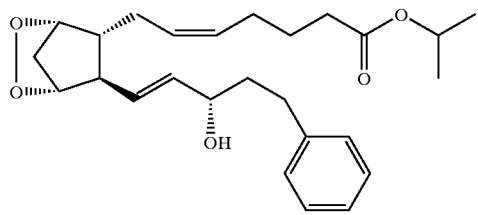

Latanoprost 13,14-dehydro-9,11-cycloendoperoxide (20)

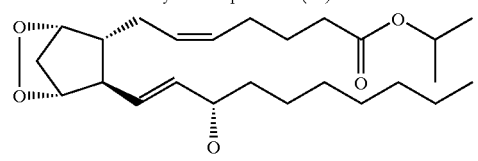

Unoprostone 13,14-dehydro-15-hydroxy-9,11-cyclodendoperoxide (21)

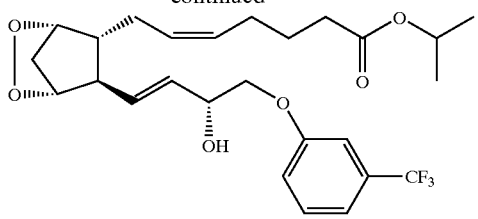

Travoprost 9,11-cycloendoperoxide (22)

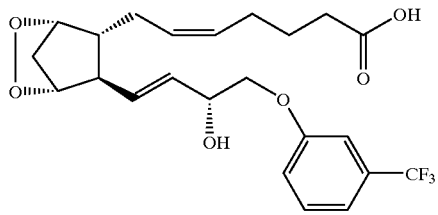

Travoprost acid 9,11-cycloendoperoxide (23)

Biological Activity, Modes of Administration

The compounds of the invention are primarily active as pro-drugs of biologically active prostaglandins or prostaglandin analogs. Because the compounds act primarily as pro-drugs their ultimate biological effect is substantially the same as that of the corresponding drug. However, because the compounds of the invention act as pro-drugs, they tend to release the corresponding drug over a period of time, and therefore are expected to act as a sustained release drug, capable of maintaining a therapeutically effective concentration of the corresponding drug for a longer period of time than the corresponding drug. Still speaking generally, pro-drugs of the present invention are likely to be administered in the same manner as the corresponding drug, and in doses comparable to the administration of the corresponding drug. For specific description of modes of administration and dosages of the known prostaglandin drugs for which the 9,11-cycloendoperoxide compounds of the invention serve as pro-drugs, reference is made to the state of the art and to U.S. Pat. Nos. 5,688,819; 5,296,504; 4,599,353; 5,422,368; 6,329,426, 5,631,287, 5,849,792, 5,889,052 and 6,011,062 the specification of all which is incorporated herein by reference.

The pro-drugs of the present invention may also be administered in combination with the corresponding drug.

An important application of several pro-drugs in accordance with the present invention is treatment of ocular hypertension or glaucoma. For this purpose, similarly to the corresponding drug, such as Bimatoprost, Latanaprost, Unoprostone, Travoprost and prostaglandin H$_2$ 1-ethanolamide, the pro-drug is preferably administered as a topical ophthalmic solution.

Still speaking generally, pharmaceutical compositions may be prepared by combining a therapeutically effective amount of at least one compound according to the present invention, or a pharmaceutically acceptable salt thereof, as an active ingredient, with conventional pharmaceutical excipients, and in some cases by preparation of unit dosage forms suitable for specific use, such as topical ocular use. The therapeutically efficient amount typically is between about 0.0001 and about 5% (w/v), preferably about 0.001 to about 1.0% (w/v) in liquid formulations.

For ophthalmic application, preferably solutions are prepared using a physiological saline solution as a major vehicle. The pH of such ophthalmic solutions should preferably be maintained between 6.5 and 7.2 with an appropriate buffer system. The formulations may also contain conventional, pharmaceutically acceptable preservatives, stabilizers and surfactants.

Preferred preservatives that may be used in the pharmaceutical compositions of the present invention include, but are not limited to, benzalkonium chloride, chlorobutanol, thimerosal, phenylmercuric acetate and phenylmercuric nitrate. A preferred surfactant is, for example, Tween 80. Likewise, various preferred vehicles may be used in the ophthalmic preparations of the present invention. These vehicles include, but are not limited to, polyvinyl alcohol, povidone, hydroxypropyl methyl cellulose, poloxamers, carboxymethyl cellulose, hydroxyethyl cellulose and purified water.

Tonicity adjustors may be added as needed or convenient. They include, but are not limited to, salts, particularly sodium chloride, potassium chloride, mannitol and glycerin, or any other suitable ophthalmically acceptable tonicity adjustor.

For ophthalmic use various buffers and means for adjusting pH may be used so long as the resulting preparation is ophthalmically acceptable. Accordingly, buffers include acetate buffers, citrate buffers, phosphate buffers and borate buffers. Acids or bases may be used to adjust the pH of these formulations as needed.

In a similar vein, an ophthalmically acceptable antioxidant for use in the present invention includes, but is not limited to, sodium metabisulfite, sodium thiosulfate, acetylcysteine, butylated hydroxyanisole and butylated hydroxytoluene.

Other excipient components which may be included in the ophthalmic preparations are chelating agents. The preferred chelating agent is edetate disodium, although other chelating agents may also be used in place or in conjunction with it.

The ingredients are usually used in the following amounts:

| Ingredient | Amount (% w/v) |
| --- | --- |
| active ingredient | about 0.001–5 |
| preservative | 0–0.10 |
| vehicle | 0–40 |
| tonicity adjustor | 1–10 |

-continued

| Ingredient | Amount (% w/v) |
| --- | --- |
| buffer | 0.01–10 |
| pH adjustor | q.s. pH 4.5–7.5 |
| antioxidant | as needed |
| surfactant | as needed |
| purified water | as needed to make 100% |

The actual dose of the active compounds of the present invention depends on the specific compound, and on the condition to be treated; the selection of the appropriate dose is well within the knowledge of the skilled artisan.

The ophthalmic formulations of the present invention may be conveniently packaged in forms suitable for metered application, such as in containers equipped with a dropper, to facilitate the application to the eye. Containers suitable for drop-wise application are usually made of suitable inert, non-toxic plastic material, and generally contain between about 0.5 and about 15 ml solution.

DESCRIPTION OF SPECIFIC EMBODIMENTS AND EXAMPLES

General Procedure A

Chemical Synthesis of Arachidonyl Ethanolamide (Compound 2)

The chemical synthesis of arachidonyl ethanolamide from arachidonic acid (Compound 1) is illustrated in Reaction Scheme 1. Arachidonyl ethanolamide (Compound 2) is synthesized following a literature procedure of Abadji et al., J. Med. Chem. 1994, 37, 1889–1893, incorporated herein by reference. To a 0.1 M solution of arachidonic acid (Compound 1, available from Cayman Chemical) in anhydrous benzene at 0° C. is added one equivalent of anhydrous dimethyl formamide and two equivalents of oxalyl chloride. The reaction is stirred at room temperature for 1 h and an equal volume of anhydrous tetrahydrofuran (THF) is added. The mixture is then cooled to 0° C. and a 1 M solution of 10 equivalents 2-amino-ethanol in anhydrous THF is added. The reaction is stirred at room temperature until completion. The reaction mixture is then diluted with chloroform, washed successively with 1 M HCl, 1 M NaOH, brine, dried over $Na_2SO_4$, and concentrated in vacuo. The crude product is purified by chromatography on silica gel. Arachidonyl ethanolamide (Compound 2) is enzymatically converted into the corresponding 9,11-cycloendoperoxide derivative as shown in Reaction Scheme 3 and is described below.

REACTION SCHEME 1

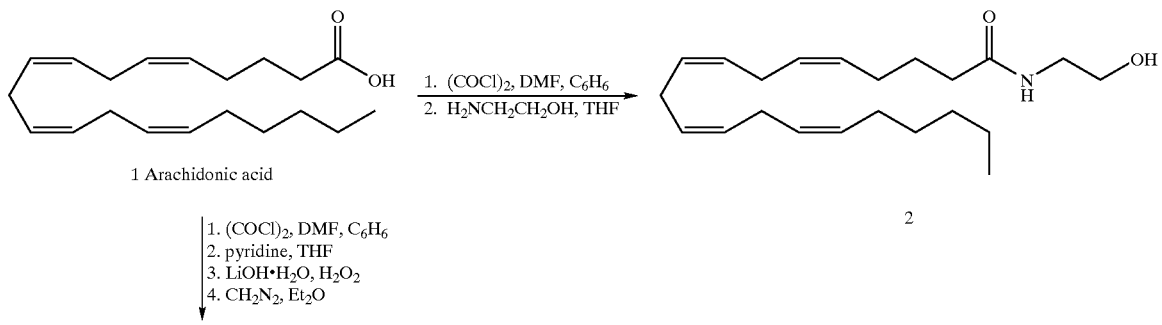

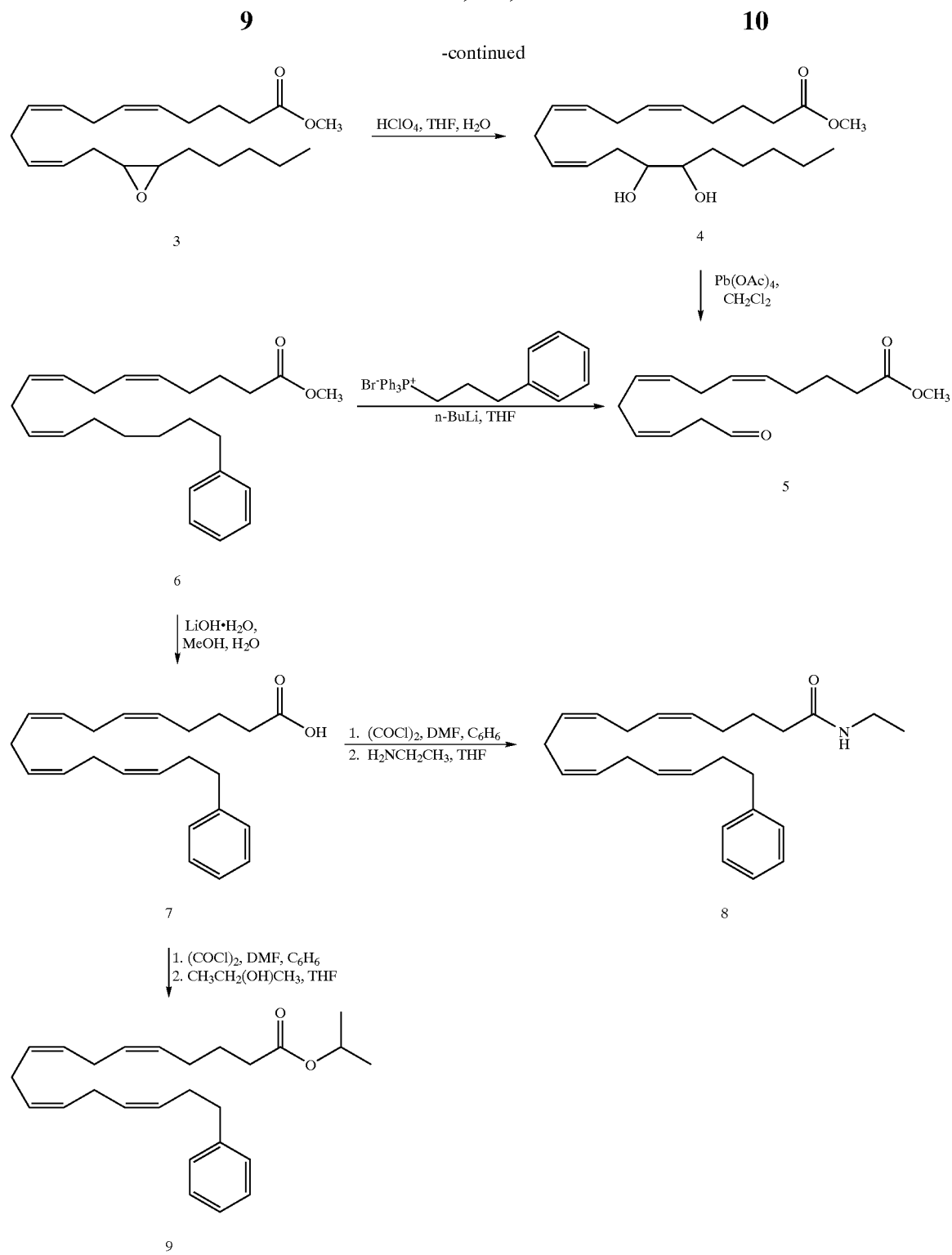

Chemical Synthesis of Compound 3

The chemical synthesis of Compound 3 from arachidonic acid (Compound 1) is also illustrated in Reaction Scheme 1. Compound 3 is synthesized by modification of procedures reported by Ryan et al. J. Med. Chem. 1997, 40, 3617–3625, based on previous work by Corey et al. Tetrahedron Lett. 1983, 24, 37–40 and Manna et al. Tetrahedron Lett. 1983, 24, 33–36. The Ryan et al., Corey et al., and Manna et al. publications are hereby expressly incorporated by reference.

To a 0.4 M solution of arachidonic acid (Compound 1) in anhydrous benzene at 0° C. are added two equivalents of oxalyl chloride. The mixture is stirred for overnight while allowed to warm to room temperature. The solvent and excess oxalyl chloride is removed in vacuo. The resulting crude acid chloride is dissolved in anhydrous THF to make a ~2 M solution. Half an equivalent of pyridine is added to the above solution and the mixture is stirred for 10 min at 0° C. 0.7 M solution of LiOH.H$_2$O in 50% H$_2$O$_2$ containing one equivalent of LiOH.H$_2$O is added and the mixture is stirred for 20 min. The reaction is quenched with pH 7 buffer and brine and extracted with CH$_2$Cl$_2$ (×3). The combined organic layer is washed with brine and dried over Na$_2$SO$_4$. During this time the epoxy acid is formed and its formation can be monitored by TLC analysis. Upon completion, the drying agent is removed by filtration and the solvent is removed in vacuo. The residue is dissolved in anhydrous Et$_2$O and treated with excess diazomethane. After stirring for 15 min, excess diazomethane is evaporated in a fume hood at room temperature and the solvent is removed in vacuo. The crude product is purified by chromatography on silica gel.

Chemical Synthesis of Compound 4

The chemical synthesis of Compound 4 from Compound 3 is also illustrated in Reaction Scheme 1. Compound 4 is synthesized following procedures reported by Ryan et al. J. Med. Chem. 1997, 40, 3617–3625. A 0.05 M solution of Compound 3 in THF—H$_2$O (2:1) is treated with five equivalents of 1.2 M HClO$_4$ at room temperature for overnight. The reaction mixture is then quenched with pH 7 buffer and extracted with EtOAc (×3). The combined organic layer is washed with brine, dried over Na$_2$SO$_4$, and concentrated in vacuo. The residue is purified by chromatography on silica gel.

Chemical Synthesis of Compound 5

The chemical synthesis of Compound 5 from Compound 4 is also illustrated in Reaction Scheme 1. Compound 5 is synthesized following procedures reported by Ryan et al. J. Med. Chem. 1997, 40, 3617–3625. A 0.2 M solution of Compound 4 in CH$_2$Cl$_2$ at −20° C. is treated with one equivalent of lead (IV) tetraacetate (0.2 M solution in CH$_2$Cl$_2$) for 0.5 h. The reaction mixture is filtered through a pad of celite-silica gel and washed with hexane. The solvent is removed in vacuo to afford Compound 5 which is unstable and is used immediately in the next reaction.

General Procedure B

Chemical Synthesis of Compound 6

The chemical synthesis of Compound 6 from Compound 5 is also illustrated in Reaction Scheme 1. Compound 6 is synthesized by Wittig olefination of Compound 5 with the ylide triphenyl-(3-phenylpropylidene)-δ$^5$-phosphane. The ylide is generated by adding one equivalent of n-butyllithium to a 0.3M solution of triphenyl-(3-phenyl-propyl)phosphonium bromide (available from Lancaster) in THF at −78° C. After stirring for 30 min, 0.7 equivalent of Compound 5 in THF is added and the reaction is warmed to room temperature and stirred for 1 h. After completion, the reaction is diluted with hexane, washed successively with pH 7 buffer, brine, dried over Na$_2$SO$_4$, and concentrated in vacuo. The crude product is purified by chromatography on silica gel.

General Procedure C

Chemical Synthesis of Compound 7

The chemical synthesis of Compound 7 from Compound 6 is also illustrated in Reaction Scheme 1. A mixture of Compound 6 and 7 equivalents of lithium hydroxide monohydrate in methanol-water (3:1) is heated to 50° C. until the reaction is complete by TLC analysis. The reaction mixture is cooled to room temperature, quenched with aqueous NH$_4$Cl and extracted with ethyl acetate (x3). The combined organic layer is washed with H$_2$O, brine, dried over Na$_2$SO$_4$, and concentrated in vacuo. The crude product is purified by chromatography on silica gel. Compound 7 is enzymatically converted into the corresponding 9,11-cycloendoperoxide derivative as shown in Reaction Scheme 4 and is described below.

Chemical Synthesis of Compound 8

Compound 8 is synthesized following General Procedure A, using ethyl amine instead of 2-amino-ethanol, as illustrated in Reaction Scheme 1. Compound 8 is enzymatically converted into the corresponding 9,11-cycloendoperoxide derivative as shown in Reaction Scheme 5 and is described below.

Chemical Synthesis of Compound 9

Compound 9 is synthesized following General Procedure A, using isopropyl alcohol instead of 2-amino-ethanol, as illustrated in Reaction Scheme 1. Compound 9 is enzymatically converted into the corresponding 9,11-cycloendoperoxide derivative as shown in Reaction Scheme 6 and is described below.

Chemical Synthesis of Compound 10

Compound 10 is synthesized by Wittig olefination following General Procedure B, using Compound 5 and (n-octyl)triphenylphosphonium bromide (available from Lancaster) instead of triphenyl-(3-phenyl-propyl) phosphonium bromide, as illustrated in Reaction Scheme 2.

Chemical Synthesis of Compound 11

Compound 11 is synthesized in a three step sequence following General Procedure C and General Procedure A, using isopropyl alcohol instead of 2-amino-ethanol as illustrated in Reaction Scheme 2. Compound 11 is enzymatically converted into the corresponding 9,11-cycloendoperoxide derivative as shown in Reaction Scheme 7 and is described below.

REACTION SCHEME 2

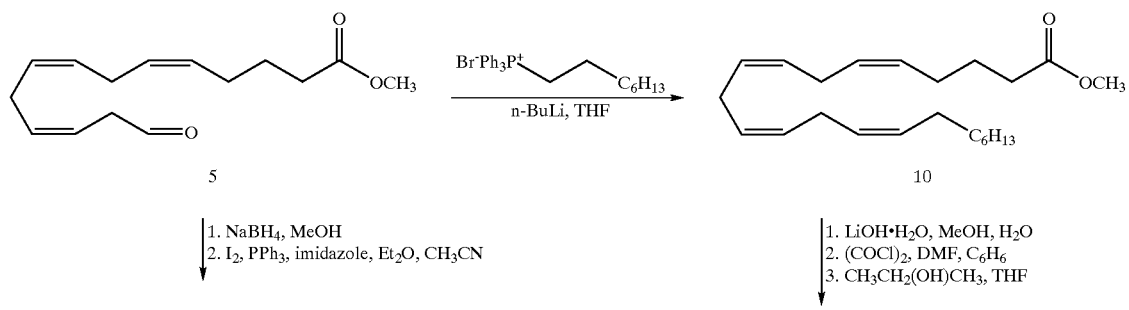

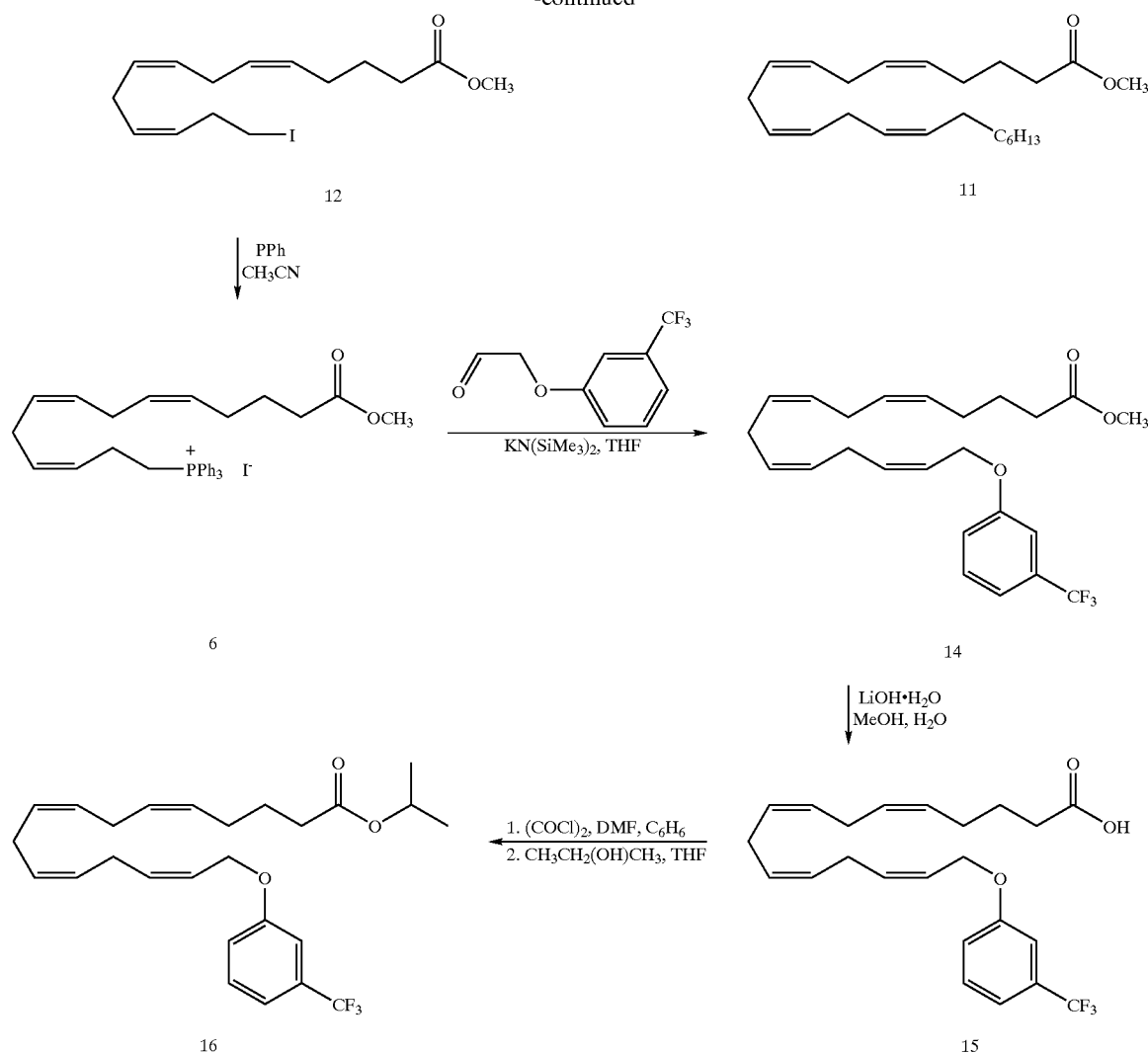

Chemical Synthesis of Compound 12

Compound 12 is synthesized from Compound 5 following procedures reported by Seltzman (Seltzman et al. J. Med. Chem. 1997, 40, 3626–3634) and Razdan (Dasse et al. Tetrahedron 2000, 56, 9195–9202), as illustrated in Reaction Scheme 2. To a 0.25 M solution of Compound 5 in methanol at 0° C. is added 2 equivalents of $NaBH_4$. The reaction is warmed to room temperature and is monitored by TLC analysis. After completion, the reaction is quenched with aqueous $NH_4Cl$ and is extracted with EtOAc (×3). The combined organic layer is washed with $H_2O$, brine, dried over $Na_2SO_4$, and concentrated in vacuo. The crude product alcohol is purified by chromatography on silica gel. This intermediate alcohol is then converted to Compound 12 following Razdan's procedures (Dasse et al. Tetrahedron 2000, 56, 9195–9202.) 1.1 equivalent of 12 is added portion-wise to a solution of 1.1 equivalent of triphenylphosphine and 1.1 equivalent of imidazole in $Et_2O$—$CH_3CN$ (3:1) at 0° C. The mixture is stirred at room temperature for 20 min, cooled to 0° C. To this mixture is added the intermediate alcohol and the reaction is stirred at room temperature for 1 h. The reaction is then diluted with pentane-$Et_2O$ (4:1), filtered through a pad of silica gel to afford Compound 12.

Chemical Synthesis of Compound 13

Compound 13 is synthesized from Compound 12 following procedures reported by Razdan (Ryan et al. J. Med. Chem. 1997, 40, 3617–3625; and Dasse et al. Tetrahedron 2000, 56, 9195–9202), as illustrated in Reaction Scheme 2. A 0.2 M solution of Compound 12 and 1.1 equivalent of triphenylphosphine in $CH_3CN$ is heated to reflux until completion of the reaction. The solvent is removed in vacuo and the residue is purified by washing with hexane-benzene (1:1). The product is dried in a vacuum oven and used directly in the next Wittig reaction.

Chemical Synthesis of Compound 14

The chemical synthesis of Compound 14 is illustrated in Reaction Scheme 2. To a 0.3 M solution of Compound 13 in THF at −78° C. is added 1 equivalent of potassium bis(trimethylsilyl)amide (available from Aldrich). The mixture is stirred at −78° C. for 30 min. A solution of 1.5 equivalent of (3-trifluoromethyl-phenoxy)-acetaldehyde (prepared by reducing 3-(trifluoromethyl)phenoxyacetonitrile (available from Lancaster) with diisobutylaluminum hydride) in THF is added dropwise to the above mixture and the reaction is gradually warmed to room temperature. Upon completion, the reaction is diluted with heaxans, washed with pH 7 buffer, brine, dried over $Na_2SO_4$, and concentrated in vacuo. The crude product is purified by chromatography on silica gel.

Chemical Synthesis of Compound 15

Compound 15 is synthesized from Compound 14 following General Procedure C as illustrated in Reaction Scheme 2. Compound 15 is enzymatically converted into the corresponding 9,11-cycloendoperoxide derivative as shown in Reaction Scheme 8 and is described below.

Chemical Synthesis of Compound 16

Compound 16 is synthesized from Compound 14 following General Procedure A, using isopropyl alcohol instead of 2-aminoethanol, as illustrated in Reaction Scheme 2. Compound 16 is enzymatically converted into the corresponding 9,11-cycloendoperoxide derivative as shown in Reaction Scheme 9 and is described below.

General Procedure D

Enzymatic Synthesis of 9,11-cycloendoperoxide of Prostaglandin $H_2$ 1-ethanolamide (Compound 17)

The human COX-2 catalyzed biosynthesis of Prostaglandin $H_2$ 1-ethanolamide 9,11-cycloendoperoxide (Compound 17) from its arachidonyl ethanolamide (Compound 2) is illustrated in Reaction Scheme 3. The enzyme human COX-2 was obtained commercially from Cayman Chemical (Ann Arbor, Mich.). It was cloned in 1992 (see the publication by Hla et al. supra). The enzyme was prepared by expression of a DNA clone encoding this enzyme in Baculovirus overexpression system in insect host cells (Sf1 cells). Ten $\mu$M [$^3$H]arachidonyl ethanolamide (Compound 2) with a specific activity of 860 $\mu$Ci/7 mg in 20 $\mu$l of ethanolic solution was diluted with 960 $\mu$l of the COX-2 (hCOX-2) reaction buffer (100 mM Tris-HCl, pH 8.0, containing 2 mM phenol, 5 $\mu$M hematin and 1 mM EDTA). One hundred units of hCOX-2 enzyme preparation in 20 $\mu$l of hCOX-2 buffer were added to start enzyme reaction. The total incubation volume was 1 ml. The enzyme reaction was stopped by adding 1 ml dry ice-cooled stop solution (ether: methanol: 1 M acetic acid, 30:4:1, v/v) immediately after incubation at 37° C. for 2 minutes. The synthesized products were extracted two times with 3 ml of ethyl acetate each. The organic phase was collected and dried at room temperature under nitrogen. The resulting residue was reconstituted in 150 $\mu$l of acetonitrile/water (1:1, v/v) for HPLC-Radiometric analysis and LC/MS/MS analysis. The LC/MS/MS analysis of the synthesized 9,11-cycloendoperoxide of prostaglandin $H_2$ 1-ethanolamide eluting at 31.6 minutes indicated that its molecular weight was 395 daltons. The yield of the synthesis as determined by HPLC-Radiometric analysis was 30%.

Enzymatic Synthesis of Bimatoprost Acid 9,11-cycloendoperoxide (Compound 18)

Bimatoprost acid 9,11-cycloendoperoxide (Compound 18) is synthesized following General Procedure D using Compound 7, instead of arachidonyl ethanolamide (Compound 2), as illustrated in Reaction Scheme 4.

Enzymatic Synthesis of Bimatoprost 9,11-cycloendoperoxide (Compound 19)

Bimatoprost 9,11-cycloendoperoxide (Compound 19) is synthesized following General Procedure D using Compound 8 instead of arachidonyl ethanolamide (Compound 2) as illustrated in Reaction Scheme 5.

REACTION SCHEME 3

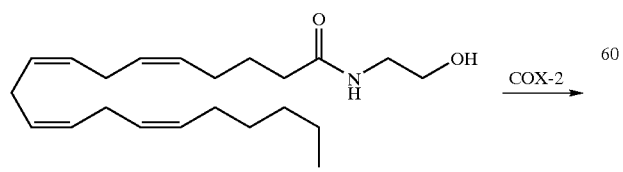

2

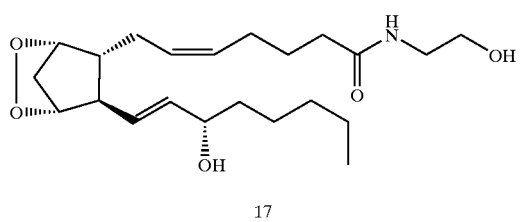

17

REACTION SCHEME 4

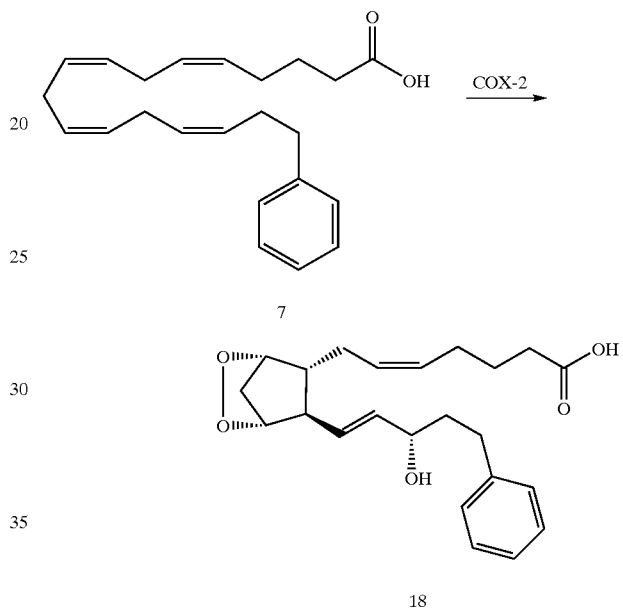

REACTION SCHEME 5

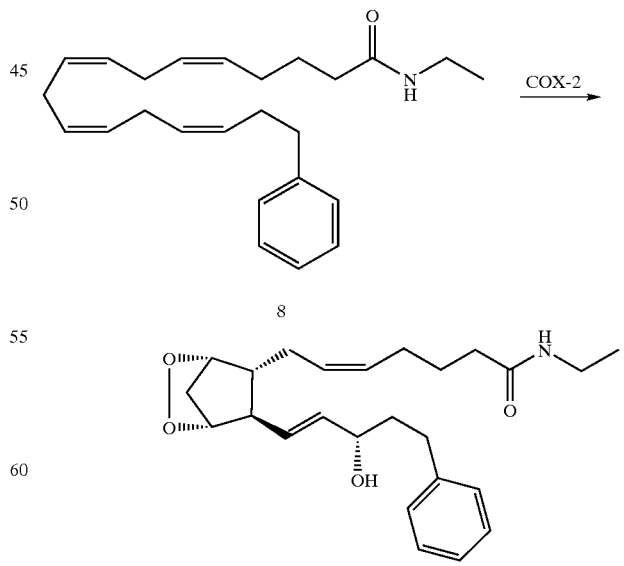

Enzymatic Synthesis of Latanoprost 13,14-dehydro-9,11-cycloendoperoxide (Compound 20)

Latanoprost 13,14-dehydro-9,11-cycloendoperoxide (Compound 20) is synthesized following General Procedure D using Compound 9 instead of arachidonyl ethanolamide (Compound 2), as illustrated in Reaction Scheme 6.

Enzymatic Synthesis of Unoprostone 15-hydroxy-9,11-cycloendoperoxide (Compound 21)

Unoprostone 15-hydroxy-9,1-cycloendoperoxide (Compound 21) is synthesized following General Procedure D using Compound 11 instead of arachidonyl ethanolamide (Compound 2) as illustrated in Reaction Scheme 7.

Enzymatic Synthesis of Travoprost 9,11-cycloendoperoxide (Compound 22)

Travoprost 9,11-cycloendoperoxide (Compound 22) is synthesized following General Procedure D using Compound 15 instead of arachidonyl ethanolamide (Compound 2) as illustrated in Reaction Scheme 8.

Enzymatic Synthesis of Travoprost acid 9,11-cycloendoperoxide (Compound 23)

Travoprost acid 9,11-cycloendoperoxide (Compound 23) is synthesized following General Procedure D using Compound 16 instead of arachidonyl ethanolamide (Compound 2) as illustrated in Reaction Scheme 9.

REACTION SCHEME 6

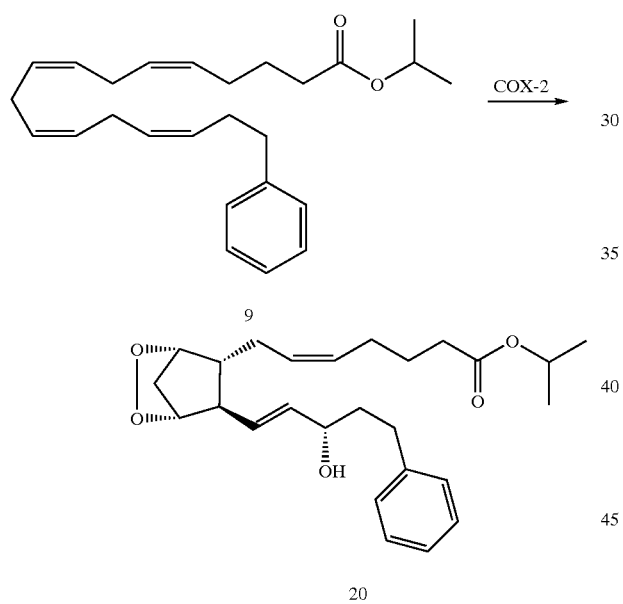

REACTION SCHEME 7

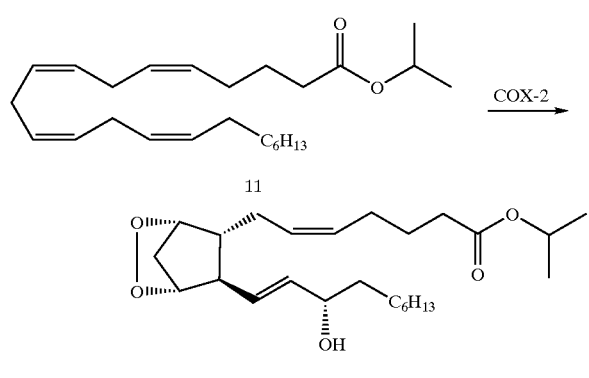

REACTION SCHEME 8

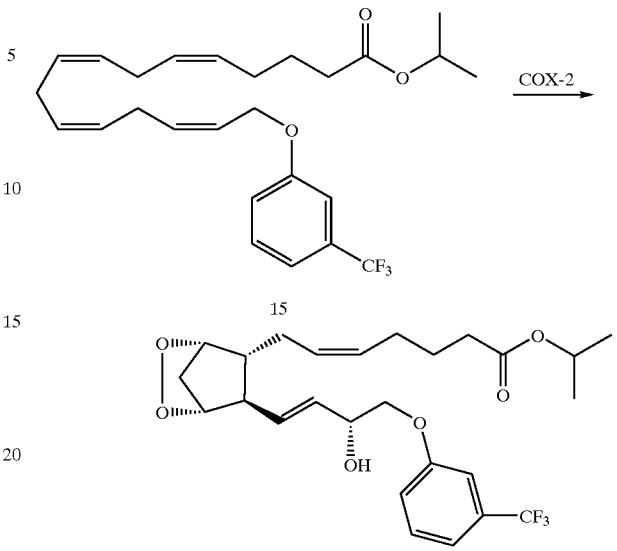

REACTION SCHEME 9

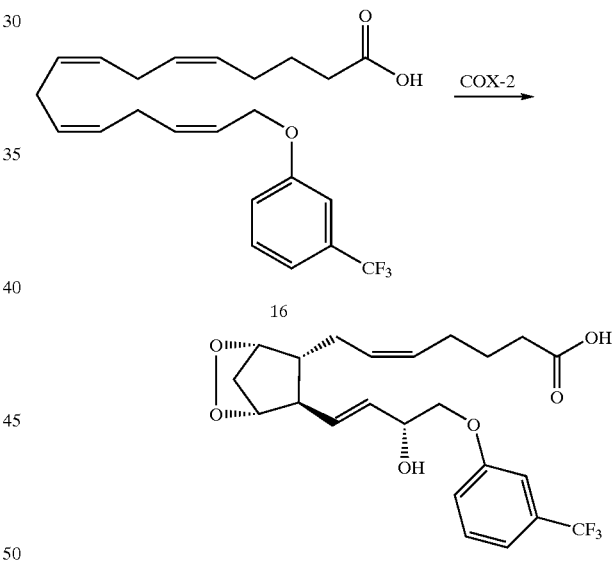

As noted above in the Summary section of the present application for patent, the 9,11-cyclopendoperoxide pro-drugs of the present invention, in addition to undergoing hydrolysis to provide the corresponding biologically active prostaglandin analogs, also act as substrates to several naturally occurring enzymes which convert the 9,11-cyclopendoperoxide pro-drugs into other biologically active analogs. Several of these enzymatic reactions which are expected to occur in vivo can be performed in vitro in accordance with the present invention resulting in the enzymatic synthesis from the 9,11-cycloendoperoxides of the invention of several biologically active prostaglandin analogs. These enzymatic reactions are illustrated below in Reaction Schemes 10 through 20.

REACTION SCHEME 10

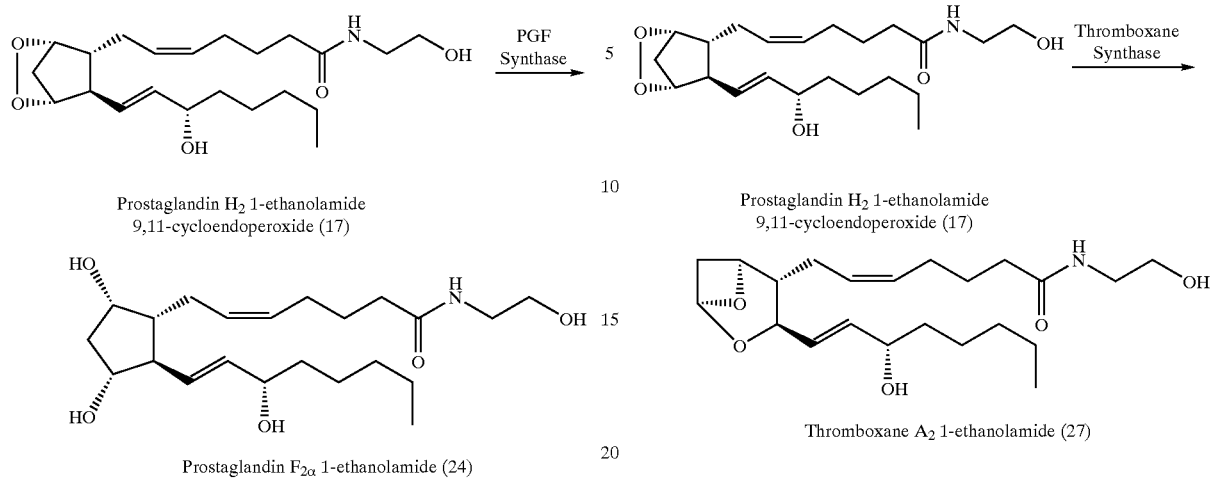

Prostaglandin H₂ 1-ethanolamide 9,11-cycloendoperoxide (17)

Prostaglandin F$_{2\alpha}$ 1-ethanolamide (24)

REACTION SCHEME 11

Prostaglandin H₂ 1-ethanolamide 9,11-cycloendoperoxide (17)

Prostaglandin E₂ 1-ethanolamide (25)

REACTION SCHEME 12

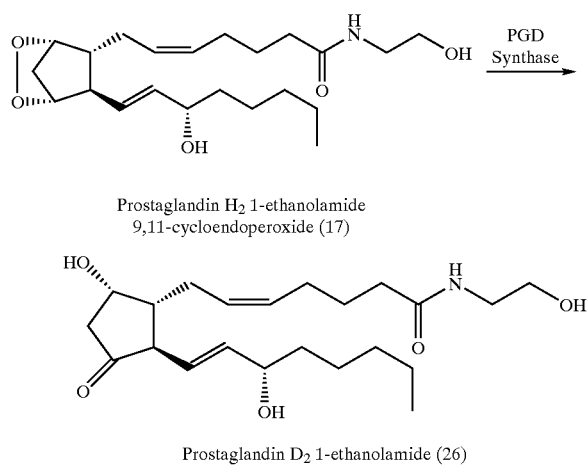

Prostaglandin H₂ 1-ethanolamide 9,11-cycloendoperoxide (17)

Prostaglandin D₂ 1-ethanolamide (26)

REACTION SCHEME 13

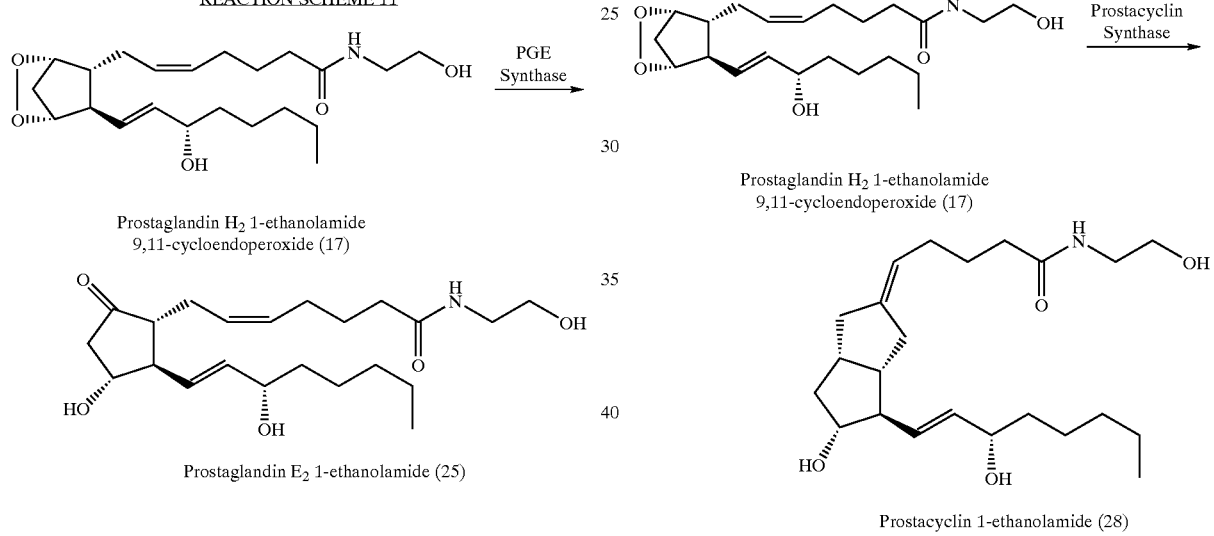

Prostaglandin H₂ 1-ethanolamide 9,11-cycloendoperoxide (17)

Thromboxane A₂ 1-ethanolamide (27)

REACTION SCHEME 14

Prostaglandin H₂ 1-ethanolamide 9,11-cycloendoperoxide (17)

Prostacyclin 1-ethanolamide (28)

General Procedure E
Enzymatic Synthesis of Prostaglandin F$_{2\alpha}$ 1-ethanolamide (Compound 24)

The human recombinant PGF synthase catalyzed biosynthesis of Prostaglandin F$_{2\alpha}$ 1-ethanolamide from prostaglandin H₂ 1-ethanolamide 9,11-cycloendoperoxide (Compound 17) is illustrated above in Reaction Scheme 10. 4.5 μM [³H]Prostaglandin H₂ 1-ethanolamide with a specific activity of 860 mCi/7 mg reconstituted in 0.6 ml of PGF synthase reaction buffer was incubated with 100 μl of the human recombinant PGF synthase solution (1.5 mg/ml) at 37° C. for 10 minutes. The cDNA clone of human PGF synthase was isolated from human lung and its enzyme was prepared by expression of cDNA clones in *E. coli* as described in the publication by Suzuki-Yamamoto et al., FEBS lett, 1999,462: 335-340, incorporated herein by reference. The plasmid was transformed into DH5$_\alpha$ *E. coli* strain and grown in LB/ampicillin medium. The expressed enzyme in *E. coli* was partially purified to yield a protein concentration of 15 mg per ml. The pUC8 vectors carrying no PGF synthase DNA insert were also transformed and prepared with protein concentration of 5 mg per ml as a negative control. The enzyme reaction was stopped by adding 1 ml dry ice-cooled stop solution (ether: methanol: 1 M acetic acid, 30:4:1, v/v) immediately after incubation at 37° C. for 10 minutes. The synthesized products were extracted with 3 ml of ethyl acetate. The organic phase was collected and dried at room temperature under nitrogen. The resulting residue was reconstituted in 150 μl of acetonitrile/water (1:1, v/v) for HPLC-Radiometric analysis and LC/MS/MS analysis. The prostaglandin $H_2$ 1-ethanolamide 9,11-cycloendoperoxide was completely converted to prostaglandin $F_{2\alpha}$ 1-ethanolamide in 10 minutes. The product ion spectrum of m/z 398.4 of the biosynthetic product was identical to the standard prostaglandin $F_{2\alpha}$1-ethanolamide. They both had the major characteristic fragment ion at m/z 62, which represents protonated 2-amino ethanol group. There was no conversion by the enzyme preparation from same $DH5_\alpha$ cells carrying pUC8 vector without PGF synthase DNA insert. The yield of the synthesis, as determined by HPLC-Radiometric analysis, was 94%.

General Procedure F
Enzymatic Synthesis of Prostaglandin $E_2$ 1-ethanolamide (Compound 25)

Prostaglandin $E_2$ 1-ethanolamide is synthesized from prostaglandin $H_2$ 1-ethanolamide 9,11-cycloendoperoxide (Compound 17) following General Procedure E using the human recombinant PGE synthase obtained in accordance with the publication of Jakobsson et al. Proc. Natl. Acad. Sci. USA, 1999, 96: 7220–7225, incorporated herein by reference, instead of the human recombinant PGF synthase, as illustrated in Reaction Scheme 11.

General Procedure G
Enzymatic Synthesis of Prostaglandin $D_2$ 1-ethanolamide (Compound 26)

Prostaglandin $D_2$ 1-ethanolamide is synthesized from its prostaglandin $H_2$ 1-ethanolamide 9,11-cycloendoperoxide (Compound 17) following General Procedure E using the human recombinant PGD synthase obtained in accordance with the publication of Nagata et al. Proc. Natl. Acad. Sci. USA, 1991, 88: 4020–4024, incorporated herein by reference, instead of the human recombinant PGF synthase, as illustrated in Reaction Scheme 12.

General Procedure H
Enzymatic Synthesis of Thromboxane $A_2$ 1-ethanolamide (Compound 27)

Thromboxane $A_2$ 1-ethanolamide is synthesized from prostaglandin $H_2$ 1-ethanolamide 9,11-cycloendoperoxide (Compound 17) following General Procedure E using the human recombinant thromboxane synthase obtained in accordance with the publication of Miyata et al., Eur. J. Biochem, 1994, 224: 273–279, incorporated herein by reference, instead of the human recombinant PGF synthase, as illustrated in Reaction Scheme 13.

General Procedure I
Enzymatic Synthesis of Prostacyclin 1-ethanolamide (Compound 28)

Prostacyclin 1-ethanolamide is synthesized from prostaglandin $H_2$ 1-ethanolamide 9,11-cycloendoperoxide (Compound 17) following General Procedure E using the human recombinant prostacyclin synthase obtained in accordance with the publication of Miyata et al., Biochem. Biophys. Res. Commun. 1994, 200: 1728–1734, instead of the human recombinant PGF synthase, as illustrated in Reaction Scheme 14. Enzymatic synthesis of Bimatoprost acid (Compound 29), its prostaglandin analogues $E_2$ and $D_2$ (Compounds 30–31), thromboxane analogue $A_2$ (Compound 32) and prostacyclin analogue (Compound 33)

Compounds 29–33 are synthesized starting with Bimatoprost acid 9,11-cycloendoperoxide (Compound 18), instead of prostaglandin $H_2$ 1-ethanolamide (Compound 17), following General Procedures E, F, G, H and I, respectively, as illustrated in Reaction Scheme 15 below.

REACTION SCHEME 15

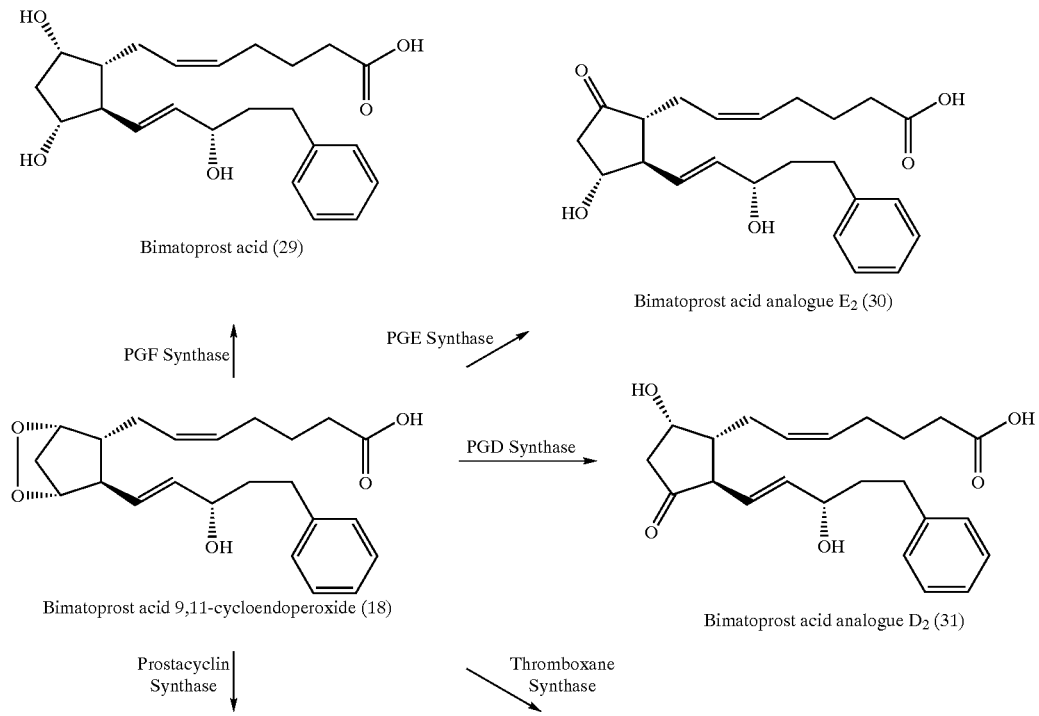

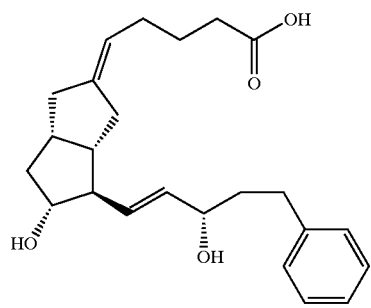

Prostacyclin analogue of Bimatoprost acid (33)

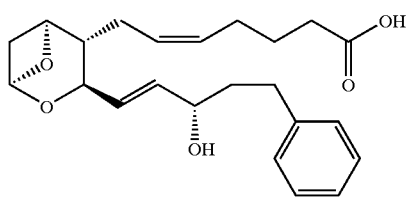

Thromboxane A₂ analogue of Bimatoprost acid (32)

Enzymatic Synthesis of Bimatoprost (Compound 34), its prostaglandin analogues E₂ and D₂ (Compounds 35–36), Thromboxane Analogue A₂ (Compound 37) and Prostacyclin Analogue (Compound 38)

Compounds 34–38 are synthesized from Bimatoprost 9,11-cycloendoperoxide (Compound 19), instead of prostaglandin H₂ 1-ethanolamide (Compound 17), following General Procedures E, F, G, H and I, respectively, as illustrated in Reaction Scheme 16 below.

REACTION SCHEME 16

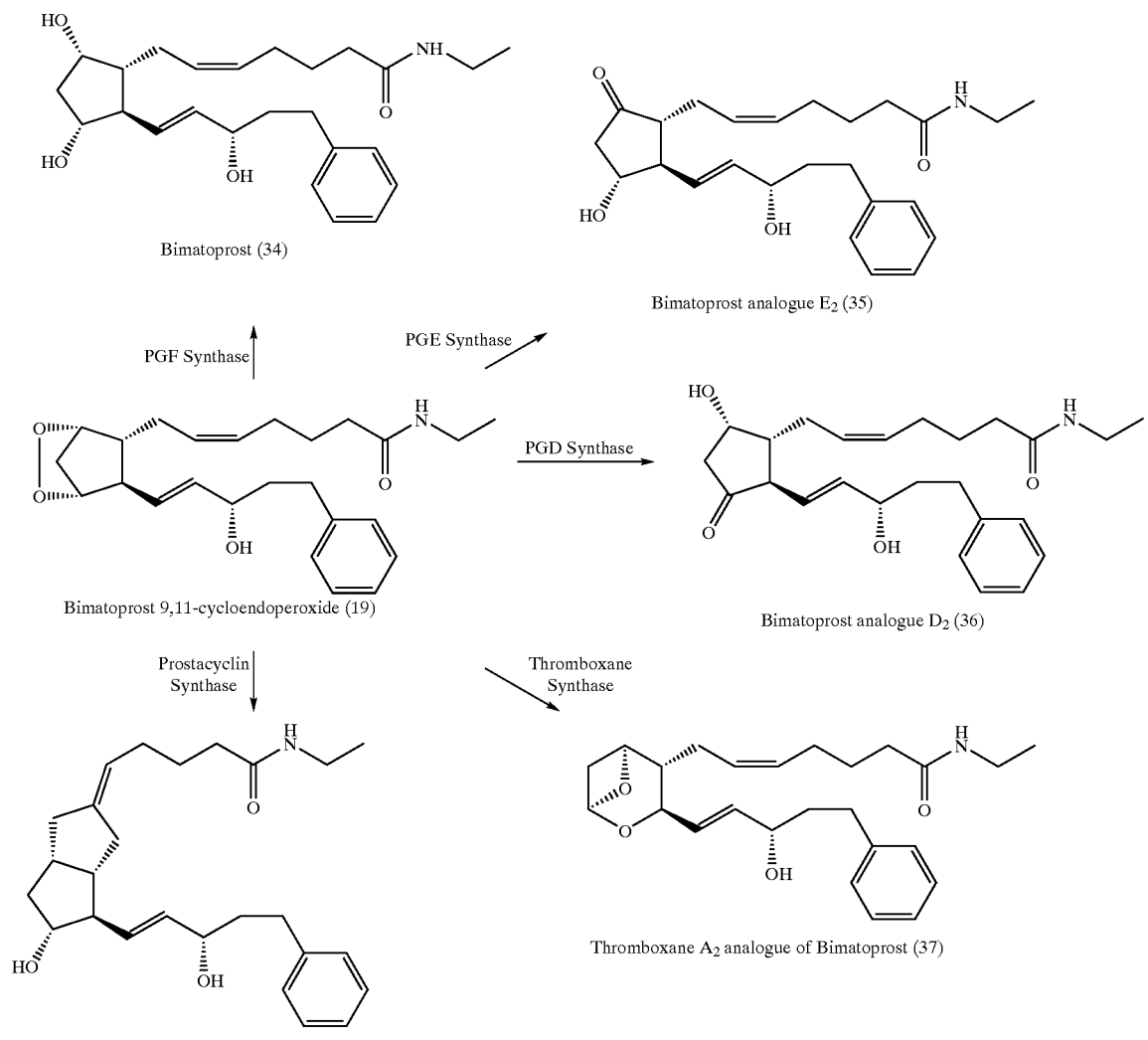

Enzymatic Synthesis of 13,14-dehydro-Latanoprost (Compound 39), its Prostaglandin Analogues $E_2$ and $D_2$ (Compounds 40–41), Thromboxane Analogue $A_2$ (Compound 42) and Prostacyclin Analogue (Compounds 43)

Compounds 39–43 are synthesized from Latanoprost 13,14-dehydro-9,11-cycloendoperoxide (Compound 20), instead of prostaglandin $H_2$ 1-ethanolamide, (Compound 17) following General Procedures E, F, G, H and I, respectively, as illustrated in Reaction Scheme 17 below.

Enzymatic Synthesis of 13,14-dehydro-15-hydro-Unoprostone (Compound 44), its Prostaglandin Analogues $E_2$ and $D_2$ (Compounds 45–46), Thromboxane Analogue $A_2$ (Compound 47) and Prostacyclin Analogue (Compound 48)

Compounds 44–48 are synthesized from Unoprostone 13,14-dehydro-15-hydroxy-9,11-cycloendoperoxide (Compound 21), instead of prostaglandin $H_2$ 1-ethanolamide (Compound 17), following General Procedures E, F, G, H and I, respectively, as illustrated in Reaction Scheme 18 below.

REACTION SCHEME 17

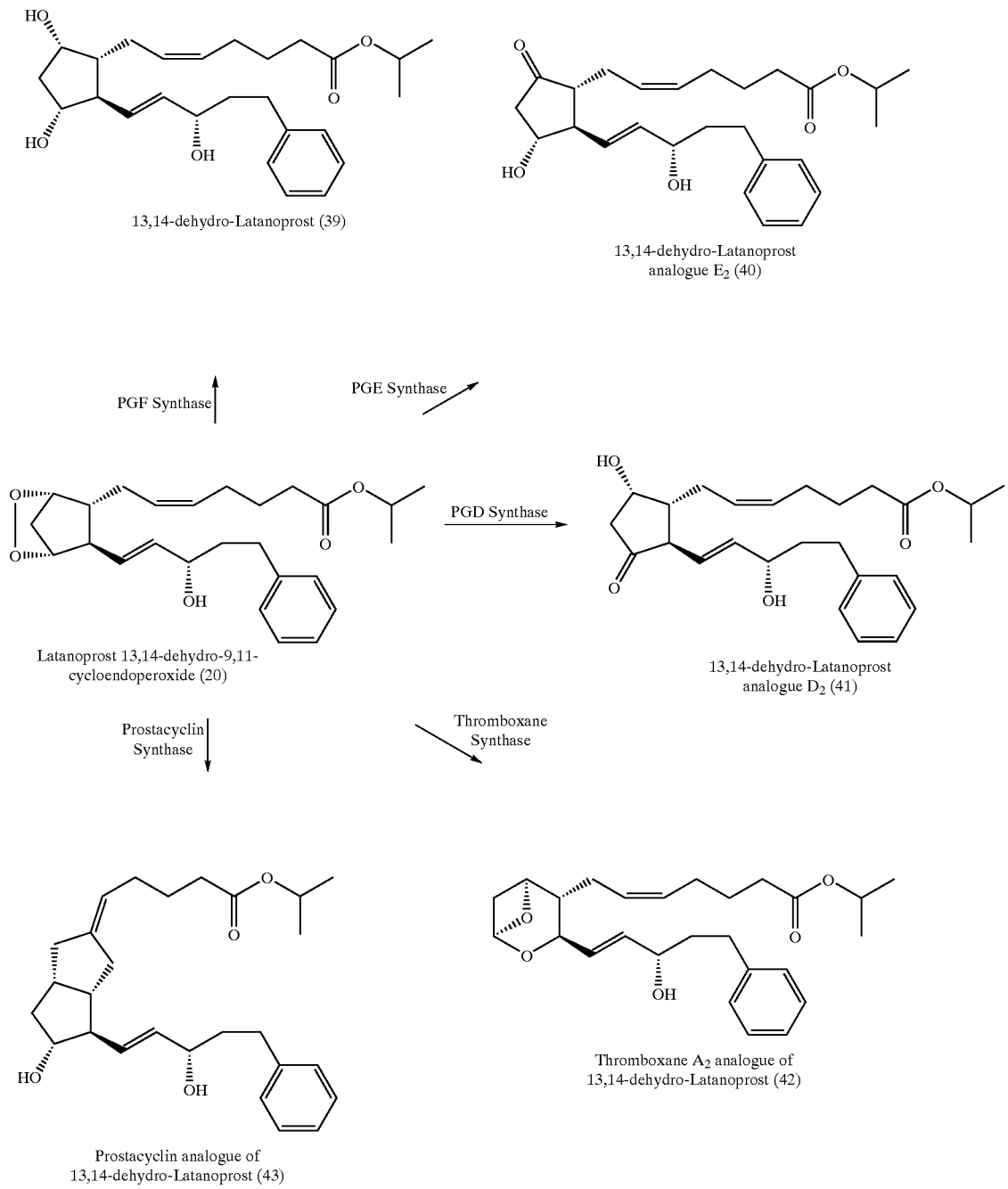

REACTION SCHEME 18

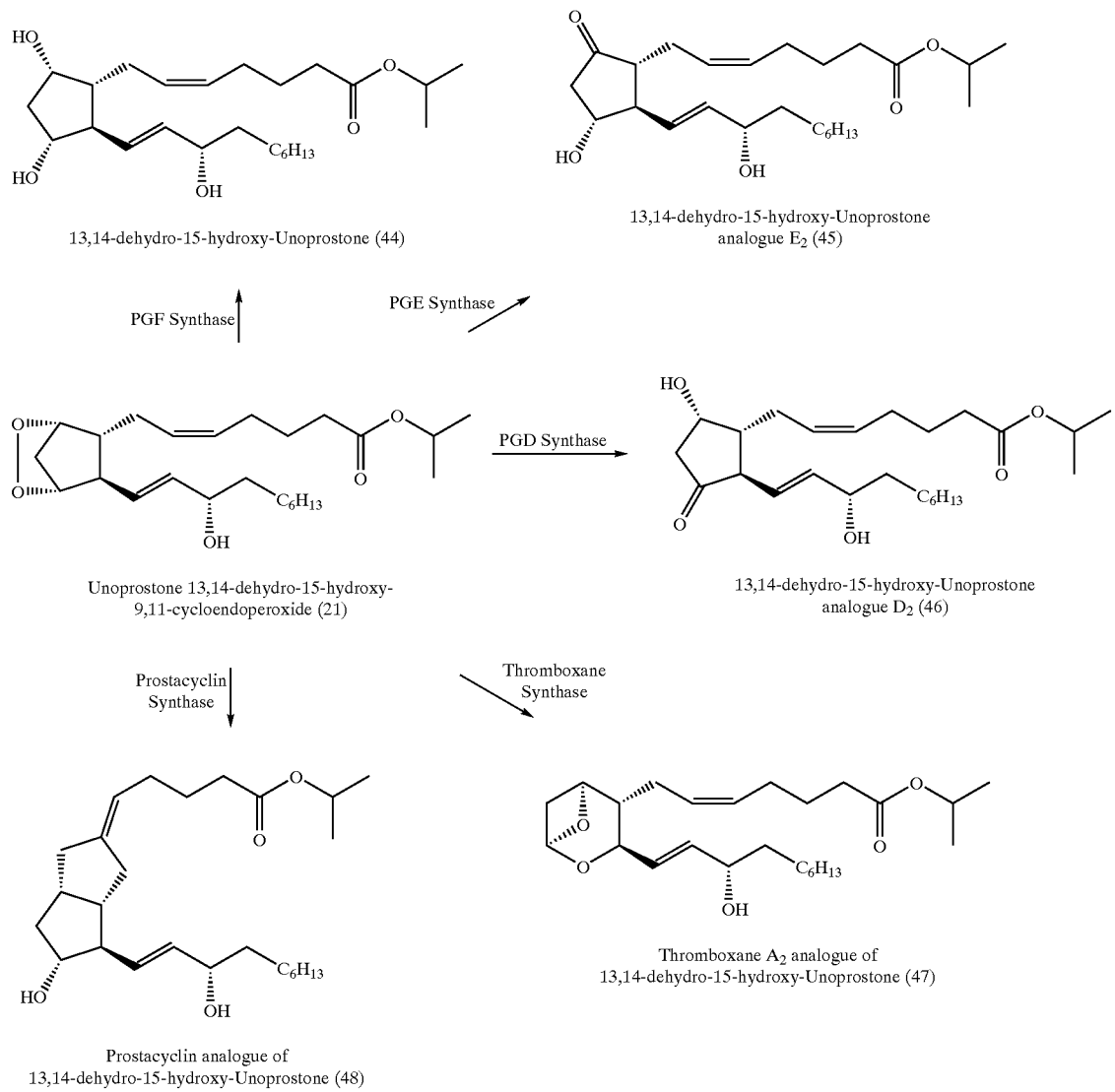

Enzymatic Synthesis of Travoprost (Compound 49), its Prostaglandin Analogues $E_2$ and $D_2$ (Compounds 50–51), thromboxane analogue $A_2$ (Compound 52) and Prostacyclin Analogue (Compound 53)

Compounds 49–53 are Synthesized from Travoprost 9,11-cycloendoperoxide (Compound 22), instead of Prostaglandin $H_2$ 1-ethanolamide (Compound 17), following General Procedures E, F, G, H and I, respectively, as illustrated in Reaction Scheme 19 below.

REACTION SCHEME 19

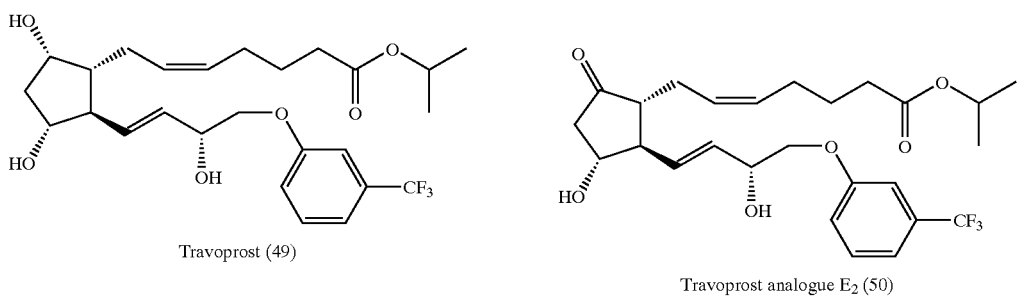

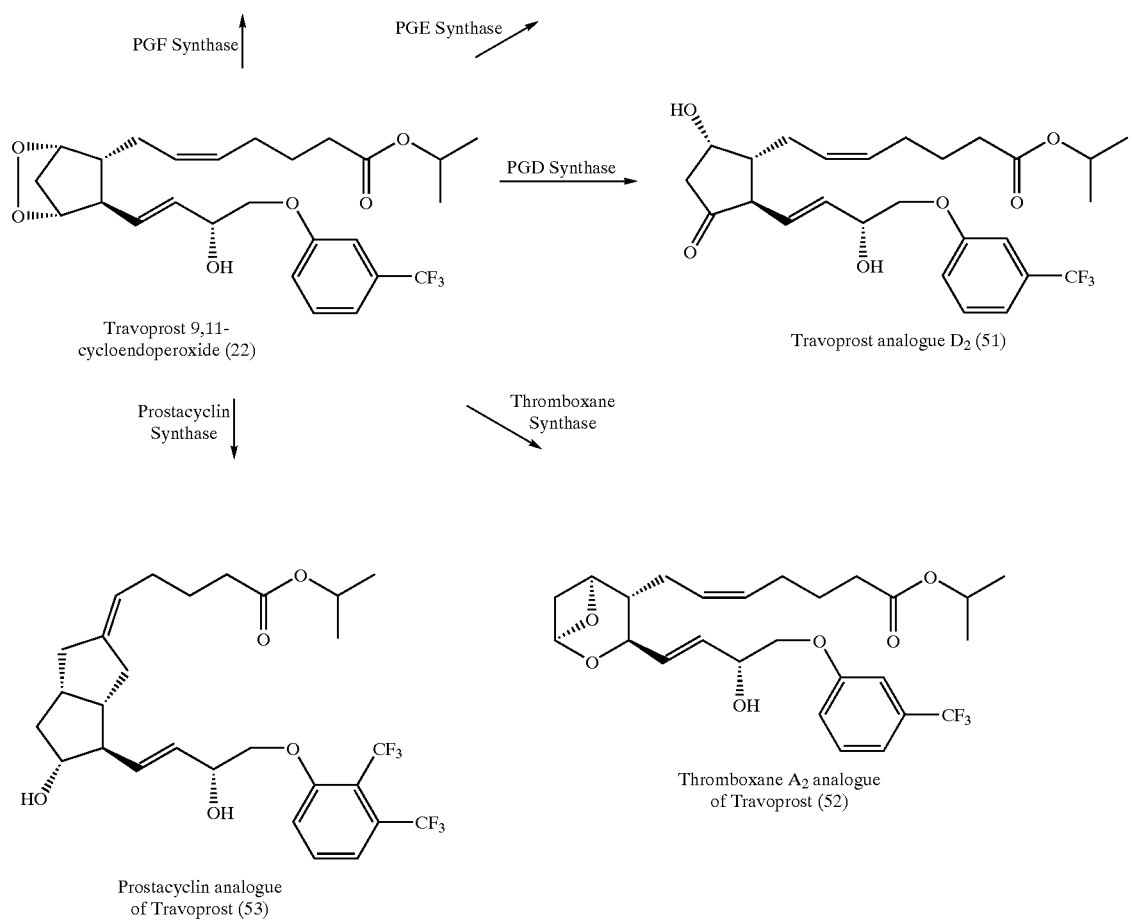

Enzymatic Synthesis of Travoprost acid (Compound 54), its Prostaglandin Analogues $E_2$ and $D_2$ (Compounds 55–56), Thromboxane Analogue $A_2$ (Compound 57) and Prostacyclin Analogue (Compounds 58)

Compounds 54–58 are synthesized from Travoprost acid 9,11-cycloendoperoxide (Compound 23), instead of prostaglandin $H_2$ 1-ethanolamide (Compound 17), following General Procedures E, F, G, H and I, respectively, as illustrated in Reaction Scheme 20 below.

REACTION SCHEME 20

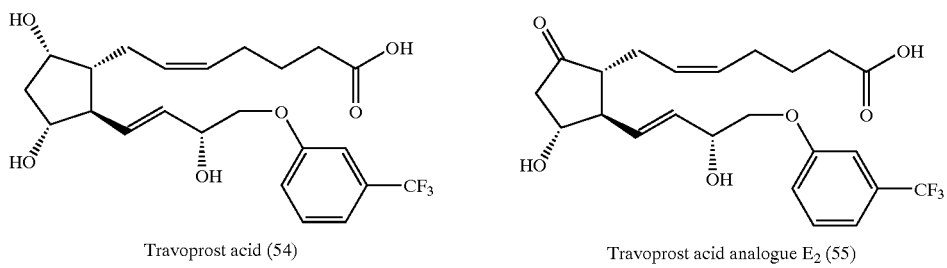

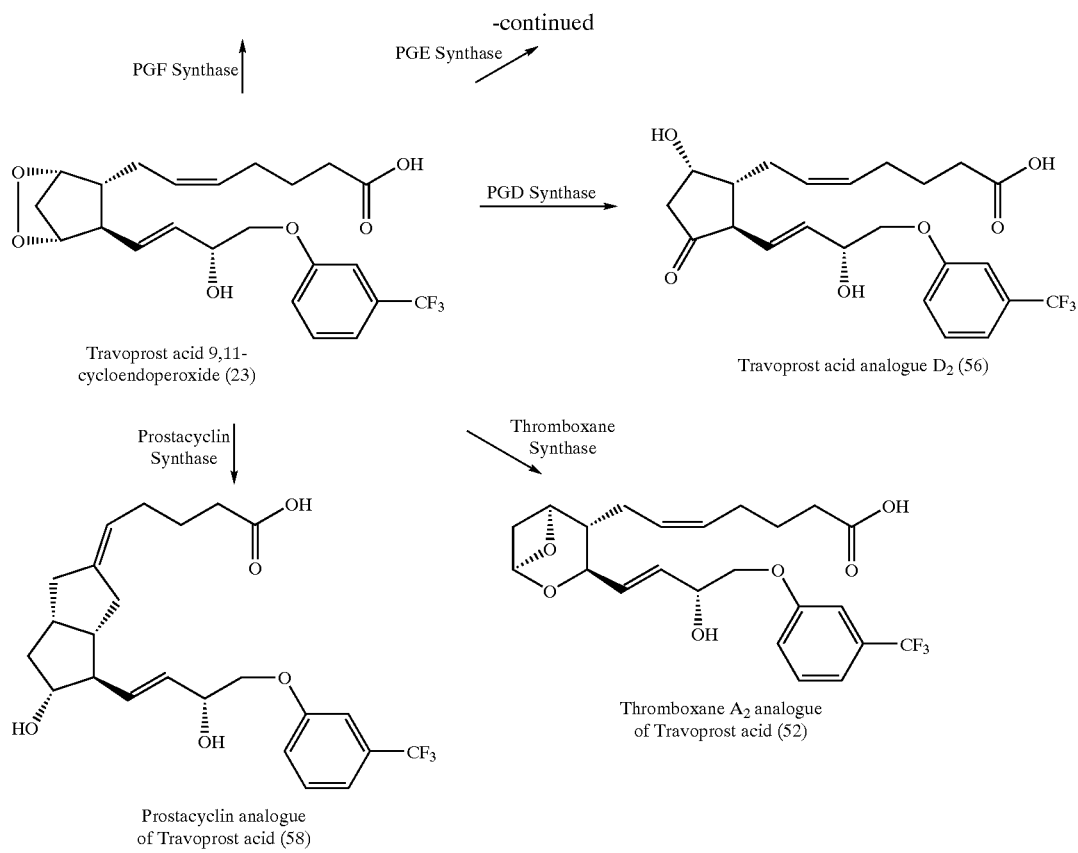

What is claimed is:
1. A compound of the formula:

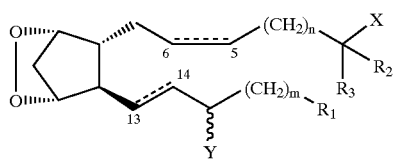

wherein the dashed lines represent the presence of a bond, or absence of a bond, wavy lines represent either alpha or beta configuration, solid triangles represent beta configuration and hatched lines represent alpha configuration;

n is an integer having the values of 1 to 6;
m is an integer having the values of 1 to 8;
X is $NH_2$, $N(R)_2$, NHR, or OR where R is hydrogen, $R_4$ or a —(CO)$R_4$ group;
Y is =S or OH, $OR_5$ or —O(CO)$R_5$ groups, said OH, $OR_5$ or O(CO)$R_5$ groups being attached to the adjacent carbon in alpha or beta configuration;
$R_1$ is H, $CH_3$, $R_7$, $OR_7$ or $SR_7$ where $R_7$ is an aliphatic, aromatic or heteroaromatic ring, said heteroaromatic ring having 1 to 3 heteroatoms selected from O, S, and N, said aliphatic, aromatic or heteroaromatic ring being optionally substituted with 1 to 3 $H_8$ groups where $H_8$ is F, Cl, Br, I, $NO_2$, $C_{1-6}$alkyl, $C_{1-6}$ fluoro substituted alkyl, COOH, or $COOR_9$ where $R_9$ is alkyl of 1 to 6 carbons or $CH_2OCH_3$;
$R_2$ and $R_3$ together represent =O, =S, or independently are hydrogen or alkyl of 1 to 6 carbon atoms, with the proviso that when X is OR then $R_1$ is not H nor methyl;
$R_4$ represents $(CH_2)_rOH$, $(CH_2)_rOCOR_9$ or $(CH_2)_rOR_9$ where r is an integer having the values 1 to 6, or $R_4$ represents saturated or unsaturated acyclic hydrocarbons having from 1 to 20 carbon atoms, or —$(CH_2)_qR_6$ where q is 0–10 and $R_6$ is an aliphatic, aromatic or heteroaromatic ring, said heteroaromatic ring having 1 to 3 heteroatoms selected from O, S, and N, said aliphatic, aromatic or heteroaromatic ring being optionally substituted with 1 to $R_8$ groups where $R_8$ is F, Cl, Br, I, $NO_2$, $C_{1-6}$alkyl, $C_{1-6}$fluoro substituted alkyl, COOH, $COOR_9$ where $R_9$ is alkyl of 1 to 6 carbons or $CH_2OCH_3$ with the further proviso that when X is NHR, m is 4 and $R_1$ is methyl then $R_4$ is not $(CH_2)_2OH$;
$R_5$ represents saturated or unsaturated acyclic hydrocarbons having from 1 to 20 carbon atoms, or —$(CH_2)_qR_6$, or a pharmaceutically acceptable salt of said compound.

2. A compound in accordance with claim 1 where n is 3.
3. A compound in accordance with claim 1 where m is an integer having the values 1 to 6.
4. A compound in accordance with claim 1 where the dotted line between the carbons designated 13 and 14 represents a bond.
5. A compound in accordance with claim 1 where the dotted line between the carbons designated 13 and 14 represents absence of a bond.
6. A compound in accordance with claim 1 where the dotted line between the carbons designated 5 and 6 represents a bond.
7. A compound in accordance with claim 1 where Y is =O or OH, or O(CO)$R_5$, where $R_5$ is alkyl of 1 to 6 carbons.
8. A compound in accordance with claim 1 where Y is OH attached to the adjacent carbon by a bond of alpha orientation.

9. A compound in accordance with claim 1 where $R_1$ is methyl, phenyl, O-phenyl, phenyl substituted with 1 to 3 $R_8$ groups, or O-phenyl substituted with 1 to 3 $R_8$ groups.

10. A compound in accordance with claim 1 where $R_2$ and $R_3$ jointly form an oxo (=O) group.

11. A compound in accordance with claim 9 where X is OH, $OR_4$ or $NHR_4$.

12. A compound in accordance with claim 10 where $R_4$ is alkyl of 1 to 6 carbons, or $(CH_2)_rOH$.

13. A compound having the formula:

where Z is O or NH;

$R_{10}$ is H, $R_{11}$ or $(CH_2)_2OH$;

$R_{11}$ is alkyl of 1 to 3 carbons, and $R_{12}$ is selected from the group consisting of n-butyl, n-hexyl, $CH_2$-phenyl and O-(3-trifluoromethyl)phenyl with the proviso that when Z is O and $R_{12}$ is n-butyl then $R_{10}$ is not H nor $R_{11}$, with the further proviso that when Z is NH and $R_{12}$ is n-butyl then $R_{10}$ is not $(CH_2)_2OH$.

14. A compound in accordance with claim 13 where Z is O.

15. A compound in accordance with claim 13 where Z is NH.

16. A compound in accordance with claim 13 where $R_{10}$ is H.

17. A compound in accordance with claim 13 where $R_{10}$ is ethyl.

18. A compound in accordance with claim 13 where $R_{10}$ is iso-propyl.

19. A compound in accordance with claim 13 where $R_{10}$ is $CH_2CH_2OH$.

20. A compound in accordance with claim 13 where $R_{12}$ is n-butyl.

21. A compound in accordance with claim 13 where $R_{12}$ is n-hexyl.

22. A compound in accordance with claim 13 where $R_{12}$ is $CH_2$-phenyl.

23. A compound in accordance with claim 13 where $R_{12}$ is O-(3-trifluoromethyl)phenyl.

24. A compound in accordance with claim 13, having the formula

25. A compound in accordance with claim 13, having the formula

26. A compound in accordance with claim 13, having

27. A compound in accordance with claim 13, having the formula

28. A compound in accordance with claim 13, having the formula

29. A compound in accordance with claim 13, having the formula

30. A pharmaceutical composition adapted for administration to a mammal, the composition comprising a pharmaceutically acceptable excipient and a compound of the formula:

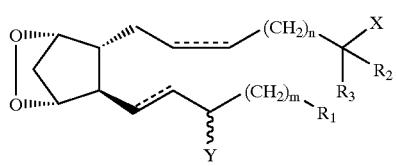

wherein the dashed lines represent the presence of a bond, or absence of a bond, wavy lines represent either alpha or beta configuration, solid triangles represent beta configuration and hatched lines represent alpha configuration;

n is an integer having the values of 1 to 6;

m is an integer having the values of 1 to 8;

X is $NH_2$, $N(R)_2$, NHR, or OR where R is hydrogen, $R_4$ or a —$(CO)R_4$ group;

Y is =O, =S or OH, $OR_5$ or —$O(CO)R_5$ groups, said OH, $OR_5$ or $O(CO)R_5$ groups being attached to the adjacent carbon in alpha or beta configuration; $R_1$ is H, $CH_3$, $R_7$, $OR_7$ or $SR_7$ where $R_7$ is an aliphatic, aromatic or heteroaromatic ring, said heteroaromatic ring having 1 to 3 heteroatoms selected from O, S, and N, said aliphatic, aromatic or heteroaromatic ring being optionally substituted with 1 to 3 $R_8$ groups where $R_8$ is F, Cl, Br, I, $NO_2$, $C_{1-6}$alkyl, $C_{1-6}$fluoro substituted alkyl, COOH, or $COOR_9$ where $R_9$ is alkyl of 1 to 6 carbons or $CH_2OCH_3$;

$R_2$ and $R_3$ together represent =O, =S, or independently are hydrogen or alkyl of 1 to 6 carbon atoms;

$R_4$ represents $(CH_2)_rOH$, $(CH_2)_rOCOR_9$ or $(CH_2)_rOR_9$ where r is an integer having the values 1 to 6, or $R_4$ represents saturated or unsaturated acyclic hydrocarbons having from 1 to 20 carbon atoms, or —$(CH_2)_qR_6$ where q is 0–10 and $R_6$ is an aliphatic, aromatic or heteroaromatic ring, said heteroaromatic ring having 1 to 3 heteroatoms selected from O, S, and N, said aliphatic, aromatic or heteroaromatic ring being optionally substituted with 1 to $R_8$ groups where $R_8$ is F, Cl, Br, I, $NO_2$, $C_{1-6}$alkyl, $C_{1-6}$fluoro substituted alkyl, COOH, $COOR_9$ where $R_9$ is alkyl of 1 to 6 carbons or $CH_2OCH_3$;

$R_5$ represents saturated or unsaturated acyclic hydrocarbons having from 1 to 20 carbon atoms, or —$(CH_2)_qR_6$, or a pharmaceutically acceptable salt of said compound.

31. A pharmaceutical composition in accordance with claim 30 which is adapted for administration to a mammal to decrease intraocular assure in the eye of the mammal.

32. A pharmaceutical composition in accordance with claim 31 wherein the compound is selected from the group consisting of compounds having the formulas (i) through (vii)

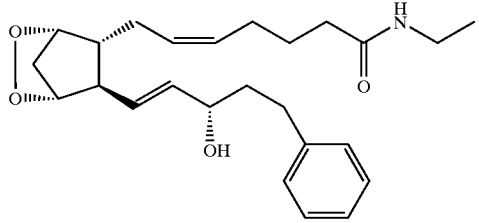
(i)

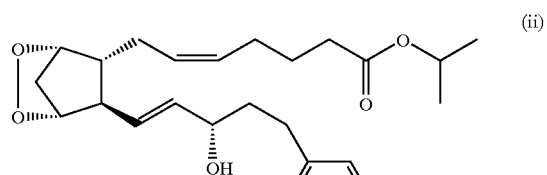
(ii)

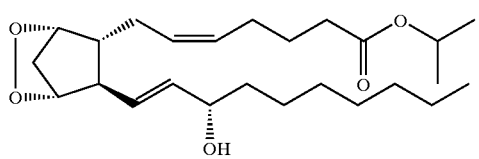
(iii)

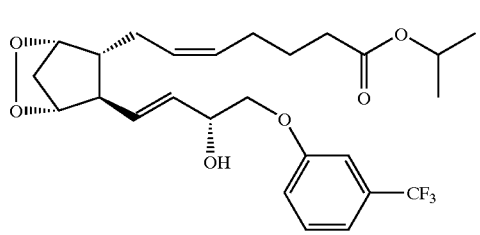
(iv)

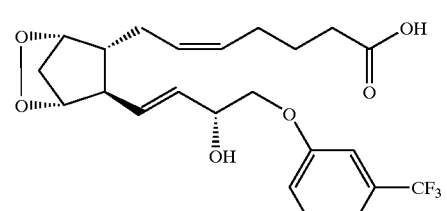
(v)

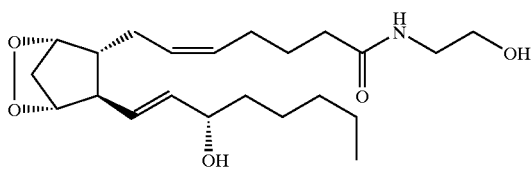
(vi)

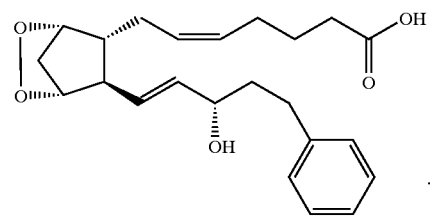
(vii)

33. A pharmaceutical composition in accordance with claim 31 adapted for topical administration to the mammalian eye.

34. A method of administering a drug to a mammal suffering from a condition selected from the group consisting of ocular hypertension, glaucoma, inflammation, gastric ulceration and blood clotting disorders comprising administering to said mammal a corresponding pro-drug compound comprising a compound of the formula

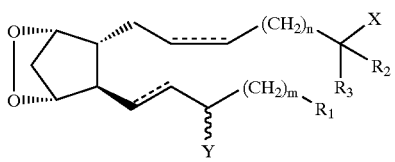

wherein the dashed lines represent the presence of a bond, or absence of a bond, wavy lines represent either alpha or beta configuration, solid triangles represent beta configuration and hatched lines represent alpha configuration;

n is an integer having the values of 1 to 6;

m is an integer having the values of 1 to 8;

X is $NH_2$, $N(R)_2$, NHR, or OR where R is hydrogen, $R_4$ or a —$(CO)R_4$ group;

Y is =O, =S or OH, $OR_5$ or —$O(CO)R_5$ groups, said OH, $OR_5$ or $O(CO)R_5$ groups being attached to the adjacent carbon in alpha or beta configuration;

$R_1$ is H, $CH_3$, $R_7$, $OR_7$ or $SR_7$ where $R_7$ is an aliphatic, aromatic or heteroaromatic ring, said heteroaromatic ring having 1 to 3 heteroatoms selected from O, S, and N, said aliphatic, aromatic or heteroaromatic ring being optionally substituted with 1 to 3 $R_8$ groups where $R_8$ is F, Cl, Br, I, $NO_2$, $C_{1-6}$alkyl, $C_{1-6}$fluoro substituted alkyl, COOH, or $COOR_9$ where $R_9$ is alkyl of 1 to 6 carbons or $CH_2OCH_3$;

$R_2$ and $R_3$ together represent =O, =S, or independently are hydrogen or alkyl of 1 to 6 carbon atoms;

$R_4$ represents $(CH_2)_rOH$, $(CH_2)_rOCOR_9$ or $(CH_2)_rOR_9$ where r is an integer having the values 1 to 6, or $R_4$ represents saturated or unsaturated acyclic hydrocarbons having from 1 to 20 carbon atoms, or —$(CH_2)_qR_6$ where q is 0–10 and $R_6$ is an aliphatic, aromatic or heteroaromatic ring, said heteroaromatic ring having 1 to 3 heteroatoms selected from O, S, and N, said aliphatic, aromatic or heteroaromatic ring being optionally substituted with 1 to $R_8$ groups where $R_8$ is F, Cl, Br, I, $NO_2$, $C_{1-6}$alkyl, $C_{1-6}$fluoro substituted alkyl, COOH, $COOR_9$ where $R_9$ is alkyl of 1 to 6 carbons or $CH_2OCH_3$;

$R_5$ represents saturated or unsaturated acyclic hydrocarbons having from 1 to 20 carbon atoms, or —$(CH_2)_qR_6$, or a pharmaceutically acceptable salt of said compound.

35. A method in accordance with claim 34 wherein the pro-drug is administered to decrease intraocular pressure in the eye of the mammal.

36. A method in accordance with claim 35 wherein the compound is selected from the group consisting of compounds having the formulas (i) through (vii):

(i)

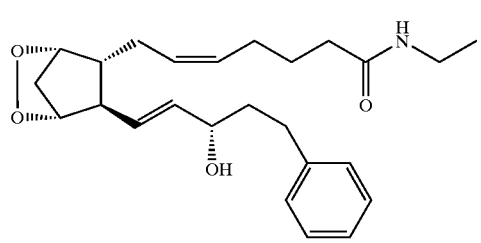

(ii)

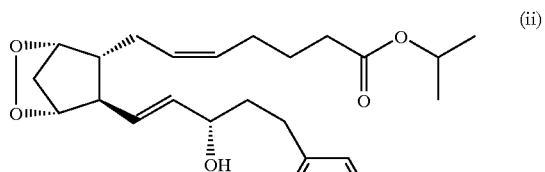

(iii)

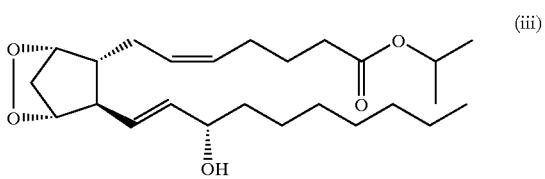

(iv)

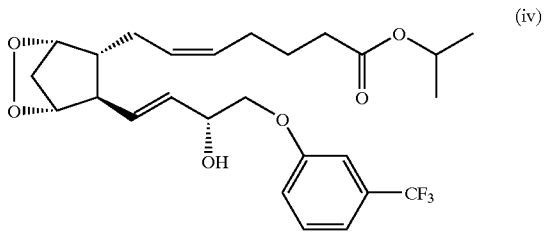

(v)

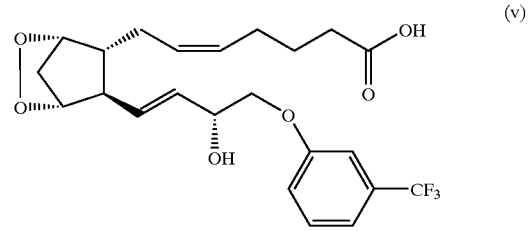

(vi)

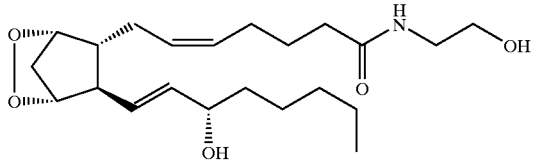

(vii)

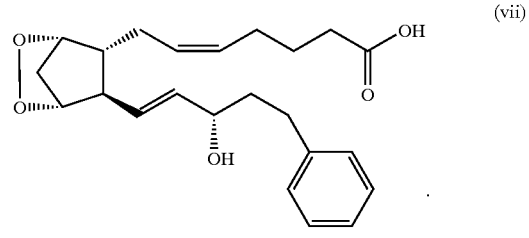

37. A method in accordance with claim 36 wherein the pro-drug is administered topically to decrease intraocular pressure in the eye of the mammal.

* * * * *

UNITED STATES PATENT AND TRADEMARK OFFICE
CERTIFICATE OF CORRECTION

PATENT NO. : 6,864,282 B2
DATED : March 8, 2005
INVENTOR(S) : Ling et al.

It is certified that error appears in the above-identified patent and that said Letters Patent is hereby corrected as shown below:

Column 5,
Line 18-27, structure 17, " 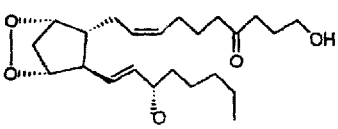

Prostaglandin $H_2$ 1-ethanolamide (17)" should be

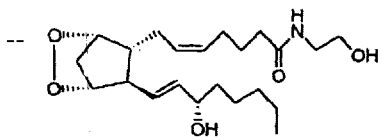

Prostaglandin $H_2$ 1-ethanolamide (17) --.

Lines 58-66, structure 21, " 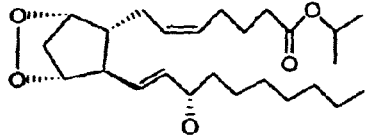

Unoprostone 13,14-dehydro-15-hydroxy-9,11-cycloendoperoxide (21)" should be

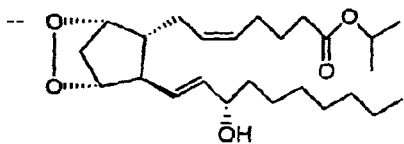

Unoprostone 13,14-dehydro-15-hydroxy-9,11-cycloendoperoxide (21) --.

Column 9,
Structure 6, " 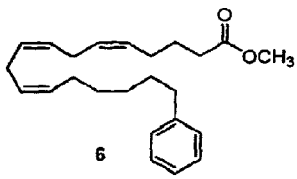 " should be -- 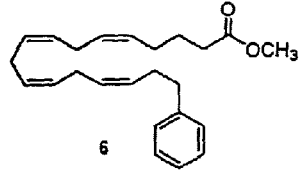 --.

Column 10,
Line 67, "$LiOH.H_2O$" should be -- $LiOH \cdot H_2O$ --.

UNITED STATES PATENT AND TRADEMARK OFFICE
CERTIFICATE OF CORRECTION

PATENT NO. : 6,864,282 B2
DATED : March 8, 2005
INVENTOR(S) : Ling et al.

It is certified that error appears in the above-identified patent and that said Letters Patent is hereby corrected as shown below:

Column 11,
Line 1, "LiOH.H$_2$0" should be -- LiOH·H$_2$0 --.

Column 13,
Line 60, "12" should be -- I$_2$ --.

Column 14,
Structure 11, " 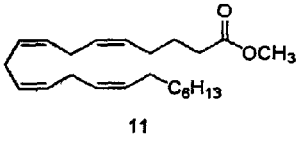 " should be -- 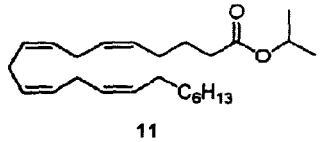 --.

Column 15,
Line 24, (Sf1 cells)." should be -- (Sf21 cells). --.

Column 17,
Line 9, "9,1" should be -- 9,11 --.

Column 32,
Reaction scheme 20, "Thromboxane A$_2$ analogue of Travoprost acid (52)" should be -- Thromboxane A$_2$ analogue of Travoprost acid (57) --.

Column 35,
Line 32, "1 to6 carbon" should be -- 1 to 6 carbon --.

Signed and Sealed this

First Day of November, 2005

JON W. DUDAS
*Director of the United States Patent and Trademark Office*